US012714666B2

(12) United States Patent
Balson et al.

(10) Patent No.: US 12,714,666 B2
(45) Date of Patent: Aug. 25, 2026

(54) ORAL DRUG DELIVERY DEVICE WITH EXPANDING ARMS

(71) Applicant: Eli Lilly and Company, Indianapolis, IN (US)

(72) Inventors: Maria Fernandez-Martos Balson, Cambridgeshire (GB); Matthew Keith Fordham, Essex (GB); Jack Alexander Hornsby, Bedfordshire (GB); Nikolaos Sotirios Vasilakis, Hertfordshire (GB); Sarah Louise Clark, Somerville, MA (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 732 days.

(21) Appl. No.: 18/245,218

(22) PCT Filed: Sep. 15, 2021

(86) PCT No.: PCT/US2021/050431

§ 371 (c)(1),
(2) Date: Mar. 14, 2023

(87) PCT Pub. No.: WO2022/060817

PCT Pub. Date: Mar. 24, 2022

(65) Prior Publication Data

US 2023/0381098 A1 Nov. 30, 2023

Related U.S. Application Data

(60) Provisional application No. 63/078,996, filed on Sep. 16, 2020.

(51) Int. Cl.

*A61K 9/00* (2006.01)
*A61M 31/00* (2006.01)

(52) U.S. Cl.

CPC ......... *A61K 9/0053* (2013.01); *A61M 31/002* (2013.01); *A61M 2210/106* (2013.01)

(58) Field of Classification Search

None

See application file for complete search history.

(56) References Cited

U.S. PATENT DOCUMENTS 7,763,014 B2 7/2010 Houzego et al.
8,147,482 B2 4/2012 Shimizu et al.

(Continued)

FOREIGN PATENT DOCUMENTS

EP 0344939 A2 * 12/1989 ........... A61K 9/2072
JP 2005-102851 A 4/2005

(Continued)

OTHER PUBLICATIONS

Mandsberg et al. "Orally ingestible medical devices for gut engineering"; Advanced Drug Delivery Reviews 142-154, (Year: 2020).*

(Continued)

*Primary Examiner* — Susan T Tran
(74) *Attorney, Agent, or Firm* — Jonathan C. Anderson

(57) ABSTRACT

The present disclosure provides a drug delivery device. The drug delivery device is taken orally by a patient, and then activates within the gastrointestinal (GI) tract of the patient. Upon activation, resilient arms within the drug delivery device expand and engage the GI tract walls. A driver then drives a plunger within the drug delivery device, pushing a drug through a channel in the resilient arms and through the GI tract walls of the patient. After a period of time, at least a portion of the drug delivery device dissolves and the drug delivery device passes through the GI tract.

38 Claims, 20 Drawing Sheets

(56) References Cited

U.S. PATENT DOCUMENTS

| | | | |
|---|---|---|---|
| 8,579,883 | B2 | 11/2013 | Tanaka et al. |
| 8,597,279 | B2 | 12/2013 | Dijksman et al. |
| 8,911,425 | B2 | 12/2014 | Dijksman et al. |
| 9,403,002 | B2 | 8/2016 | Imran et al. |
| 9,492,378 | B2 | 11/2016 | Imran |
| 9,687,638 | B2 | 6/2017 | Zou et al. |
| 9,744,139 | B2 | 8/2017 | Dijksman et al. |
| 9,878,094 | B2 | 1/2018 | Dijksman et al. |
| 10,046,109 | B2 | 8/2018 | Zou et al. |
| 10,172,598 | B2 | 1/2019 | Amaoko-Tuffour et al. |
| 10,369,111 | B2 | 8/2019 | Kabadi et al. |
| 10,376,471 | B2 | 8/2019 | Puckett |
| 10,537,720 | B2 | 1/2020 | Ben-Tsur |
| 2007/0123809 | A1 | 5/2007 | Weiss et al. |
| 2008/0063703 | A1 | 3/2008 | Gross et al. |
| 2008/0188837 | A1 | 8/2008 | Belsky et al. |
| 2011/0106063 | A1 | 5/2011 | Dijksman et al. |
| 2013/0274659 | A1 | 10/2013 | Imran et al. |
| 2015/0064241 | A1 | 3/2015 | Conrad |
| 2015/0352343 | A1 | 12/2015 | Hafezi et al. |
| 2016/0015648 | A1 | 1/2016 | Gross et al. |
| 2017/0028183 | A1 | 2/2017 | Nelson et al. |
| 2017/0258833 | A1 | 9/2017 | Imran et al. |
| 2018/0070857 | A1 | 3/2018 | Jones et al. |
| 2019/0321613 | A1 | 10/2019 | Jones et al. |
| 2020/0094031 | A1 | 3/2020 | Jones et al. |
| 2022/0039686 | A1 | 2/2022 | Arrick et al. |

FOREIGN PATENT DOCUMENTS

| | | | |
|---|---|---|---|
| WO | 2011/079302 | A | 6/2011 |
| WO | 2011-112229 | A2 | 9/2011 |
| WO | 2014/039951 | A1 | 3/2014 |
| WO | 2015/176031 | A2 | 11/2015 |
| WO | 2017/004623 | A1 | 1/2017 |
| WO | 2018/112245 | A1 | 6/2018 |
| WO | 2018/182612 | A1 | 10/2018 |
| WO | 2018/213576 | A1 | 11/2018 |
| WO | 2019/023346 | A1 | 1/2019 |
| WO | 2019/094521 | A1 | 5/2019 |
| WO | 2019/222572 | A1 | 11/2019 |
| WO | 2020-035857 | A1 | 2/2020 |
| WO | 2020/041774 | A1 | 2/2020 |
| WO | 2020/068842 | A1 | 4/2020 |
| WO | 2020-157324 | A1 | 8/2020 |
| WO | 2021/228826 | A1 | 11/2021 |
| WO | 2022/035750 | A1 | 2/2022 |
| WO | 2022/056108 | A1 | 3/2022 |
| WO | 2022/069605 | A1 | 4/2022 |
| WO | 2022/069606 | A1 | 4/2022 |
| WO | 2022/069691 | A1 | 4/2022 |

OTHER PUBLICATIONS

International Search Report of the International Searching Authority pertaining to International Application No. PCT/US2021/050431; Date of Mailing: Mar. 21, 2022; 8 pages.

Written Opinion of the International Searching Authority pertaining to International Application No. PCT/US2021/050431; Date of Mailing: Mar. 21, 2022; 12 pages.

Abramson, et al, “A luminal unfolding microneedle injector for oral delivery of macromolecules”, Nature Medicine, vol. 25, Oct. 2019, pp. 1512-1518.

* cited by examiner

A1
344
350
330
340
217
360
342
310
213
215
400
210
450
250
230
100

260
340
350
330
310
500
215
A1
217

100
110
266
264
260
350
330
310
215
220
500
A1

106
900
200
104

106
900
200
104

106
900
200
104

106
900
200
104

106
900
200
104

ORAL DRUG DELIVERY DEVICE WITH EXPANDING ARMS

FIELD OF THE DISCLOSURE

The present disclosure relates to an oral drug delivery device. More specifically, the present disclosure relates to an oral drug delivery device with expanding arms that activates within the small intestine to deliver a drug through the gastrointestinal wall.

BACKGROUND OF THE DISCLOSURE

For patients being treated with a drug or some other biologically active compound, it is often most convenient to receive the compound orally. However, the nature of some compounds prevents them from maintaining their activity once consumed. For example, some compounds are denatured, digested, or otherwise deactivated once placed in the environment of the gastrointestinal (GI) system. Additionally, some compounds have low rates of diffusion into the bloodstream from the GI system, which can prevent adequate dosages from being delivered to the patient. For compounds with these characteristics, patients often receive the compounds through injection, which is painful and inconvenient. Accordingly, it is desirable to develop an oral drug delivery device that can successfully deliver a drug that would otherwise be ineffective when taken orally.

SUMMARY

The present disclosure provides a drug delivery device. The drug delivery device is taken orally by a patient, and then activates within the gastrointestinal (GI) tract of the patient. Upon activation, arms within the drug delivery device expand, and penetrating tips penetrate the GI tract. A driver then drives a plunger within the drug delivery device, pushing a drug through the penetrating tips and through the GI tract walls of the patient. After a period of time, at least part of the drug delivery device dissolves and the drug delivery device passes through the GI tract.

In an exemplary embodiment, a drug delivery device is disclosed including a capsule configured to degrade within a gastrointestinal (GI) tract of a patient; a drug delivery mechanism within the capsule and configured to interact with a GI tract wall of the patient, the drug delivery mechanism including a plurality of resilient arms, a plurality of GI tract wall interfacing ends, and a plurality of drug delivery channels, wherein the plurality of GI tract wall interfacing ends are fluidly coupled to the plurality of drug delivery channels; a drug housing fluidly coupled to the drug delivery mechanism and configured to contain a volume of a drug; and a driving mechanism coupled to the drug housing, the driving mechanism including a stopper, a trigger, and a driver, wherein the driving mechanism actuates delivery of the drug through the drug delivery mechanism.

In another embodiment, a drug delivery device is disclosed including a degradable capsule; a drug delivery mechanism located within the degradable capsule including a fluid channel and a plurality of drug delivery members; a drug housing fluidly coupled to the fluid channel configured to hold a volume of a drug; and a driving mechanism coupled to and located at least partially within the drug housing, the driving mechanism including: a drug housing cap configured to fluidly seal the drug housing; a driving rod slidable within the drug housing; a driving stopper coupled to the driving rod configured to interface with the drug; a driver within the drug housing cap and coupled to the driving rod; a dissolvable trigger configured retain the driving rod in a first position, wherein the driver pushes the driving rod from the first position to a second position when the dissolvable trigger degrades, the drug being released through the drug delivery mechanism when the driving rod moves from the first position to the second position.

In yet another embodiment, an oral drug delivery device is disclosed including a housing capsule; a drug delivery mechanism within the housing capsule including: at least one drug delivery member configured to interact with a wall of a gastrointestinal tract of a patient; a fluid channel within the at least one drug delivery member configured to allow a drug to flow through the drug delivery member, wherein a fluid resistance within the fluid channel is greater than an interstitial resistance from an interaction with the wall of the gastrointestinal tract; a drug housing coupled to the drug delivery mechanism; and a driving mechanism configured to drive a drug from the drug housing to the drug delivery mechanism.

In still yet another embodiment, an oral drug delivery device is disclosed including a biodegradable capsule, a plurality of arms, and a liquid drug, wherein the oral drug delivery device has a closed configuration in which the plurality of arms is disposed within the capsule, an open configuration in which the plurality of arms extend radially outward upon degradation of the capsule to contact a patient, a delivered configuration in which the liquid drug is injected through the plurality of arms and into the patient, and a released configuration in which the plurality of arms is separated from the patient to pass through the patient.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
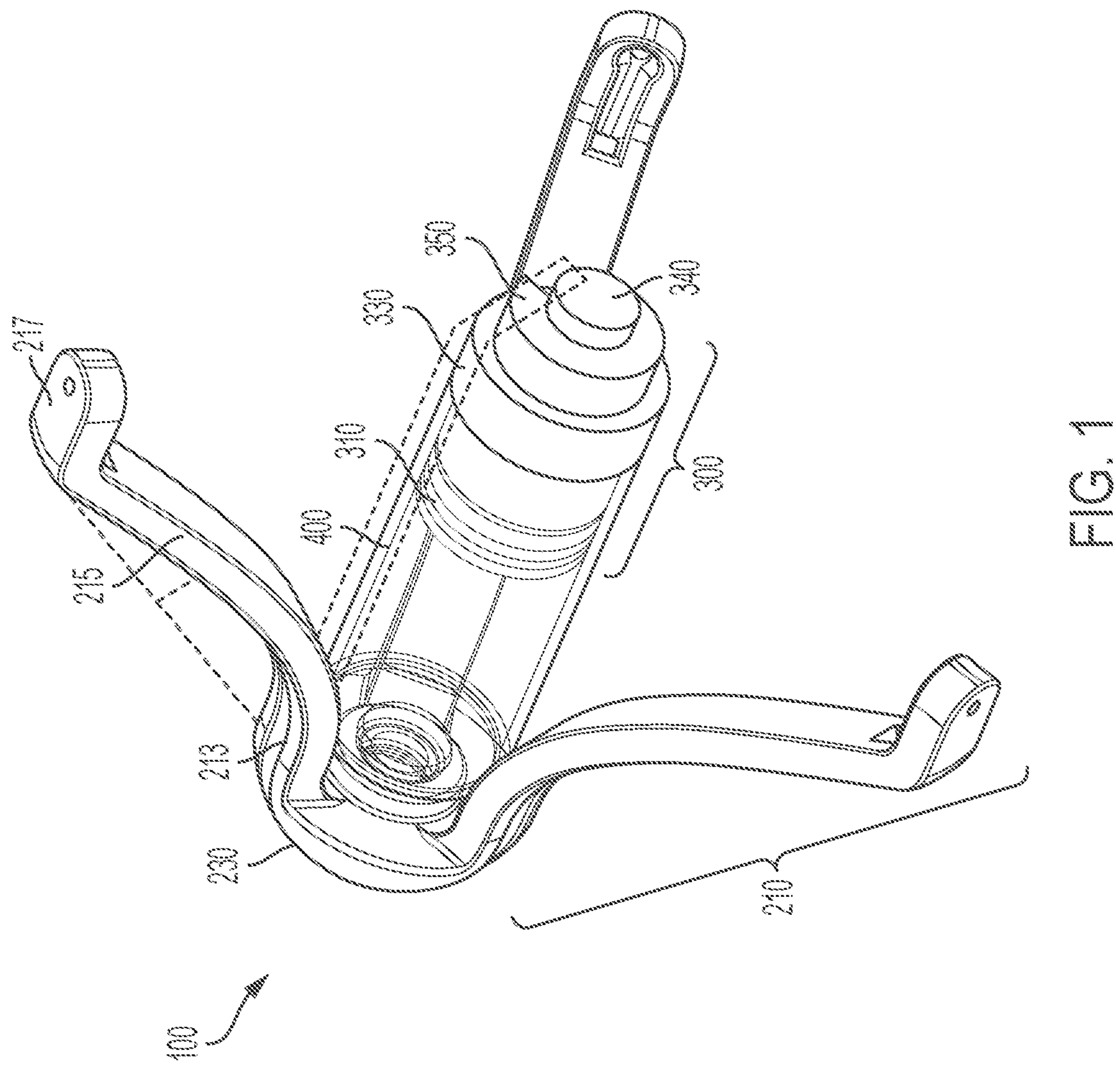
FIG. 1 is a perspective view of an exemplary embodiment of a drug delivery device according to the present disclosure.

First referring to FIGS. 1-6, a drug delivery device 100 is shown. Drug delivery device 100 comprises a capsule 110, a delivery mechanism 200, a driving mechanism 300, and a drug housing 400. Drug housing 400 may also be referred to as a cartridge. When the drug delivery device 100 is fully assembled, the capsule 110 encloses the delivery mechanism 200, driving mechanism 300, and drug housing 400. As discussed in greater detail herein, drug delivery device 100 is configured to be taken orally by a patient. Upon entering a portion of the gastrointestinal (GI) tract of the patient, the capsule 110 degrades or otherwise breaks apart and thereby allows delivery mechanism 200 to interact with the interior wall of the GI tract and secure drug delivery device 100 in place. Once the delivery mechanism 200 has interacted with the patient's GI tract, the driving mechanism 300 actuates the delivery of a drug 500 from the drug housing 400 to the patient through the GI tract wall. Once the drug 500 has been delivered, the drug delivery device 100 passes through the GI tract.

Figure 2:
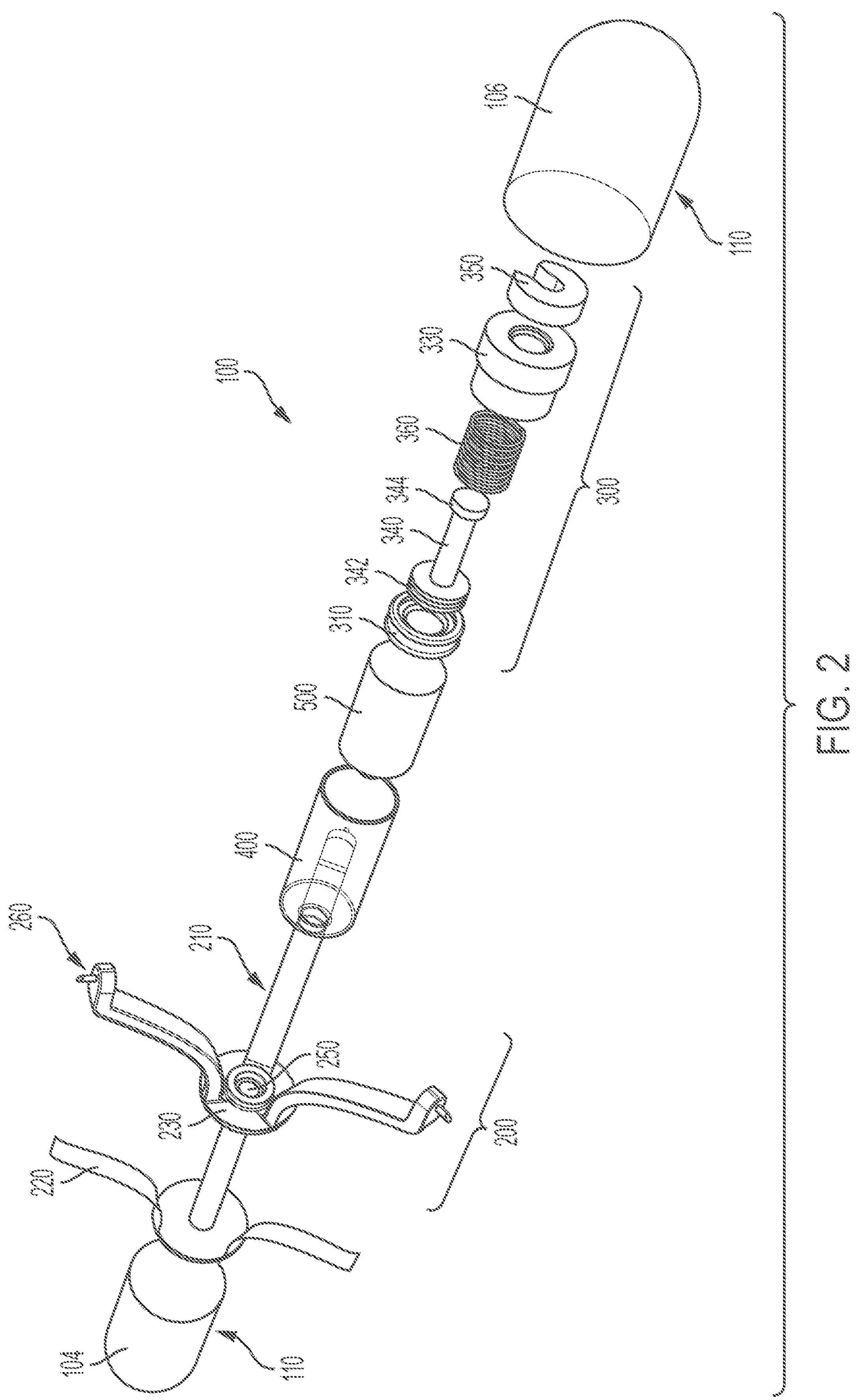
FIG. 2 is an exploded perspective view of the drug delivery device of FIG. 1.
Figure 3:
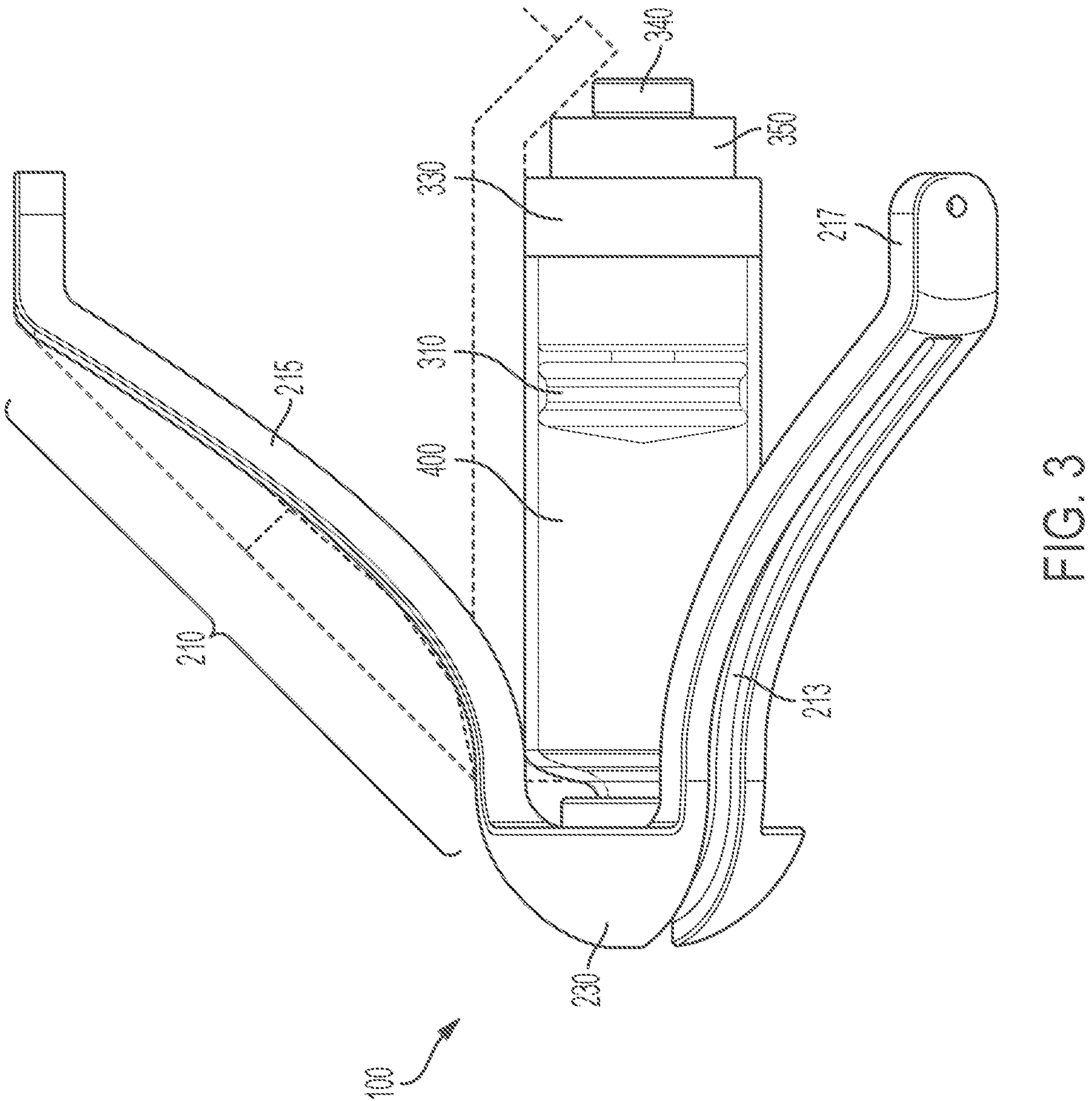
FIG. 3 is a right elevational view of the drug delivery device of FIG. 1.
Figure 4:
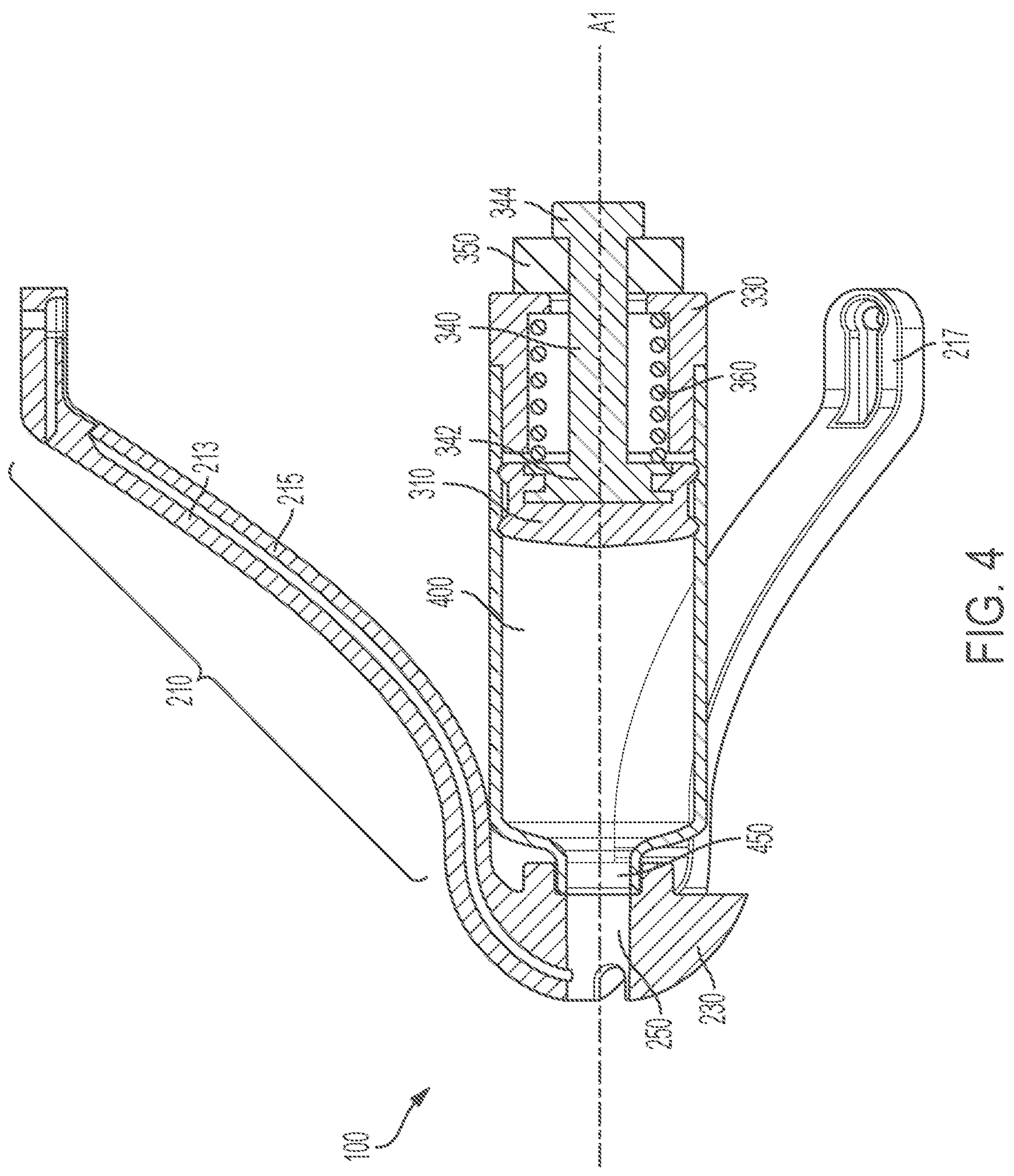
FIG. 4 is a right cross-sectional view of the drug delivery device of FIG. 1.
Figure 6:
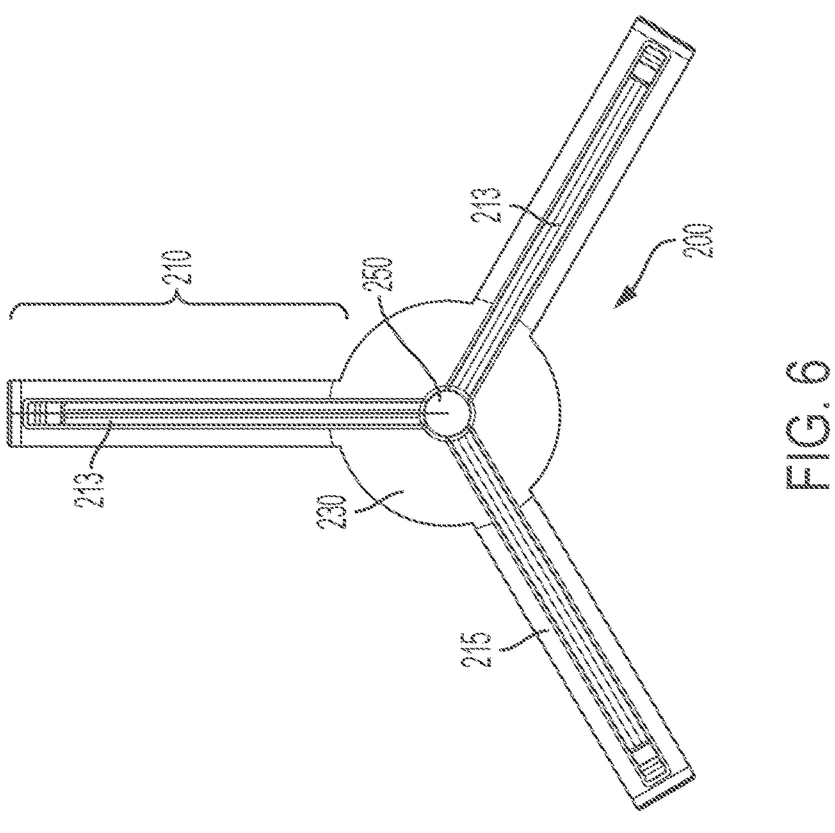
FIG. 6 is a rear elevational view of the drug delivery device of FIG. 1.
Figure 5:
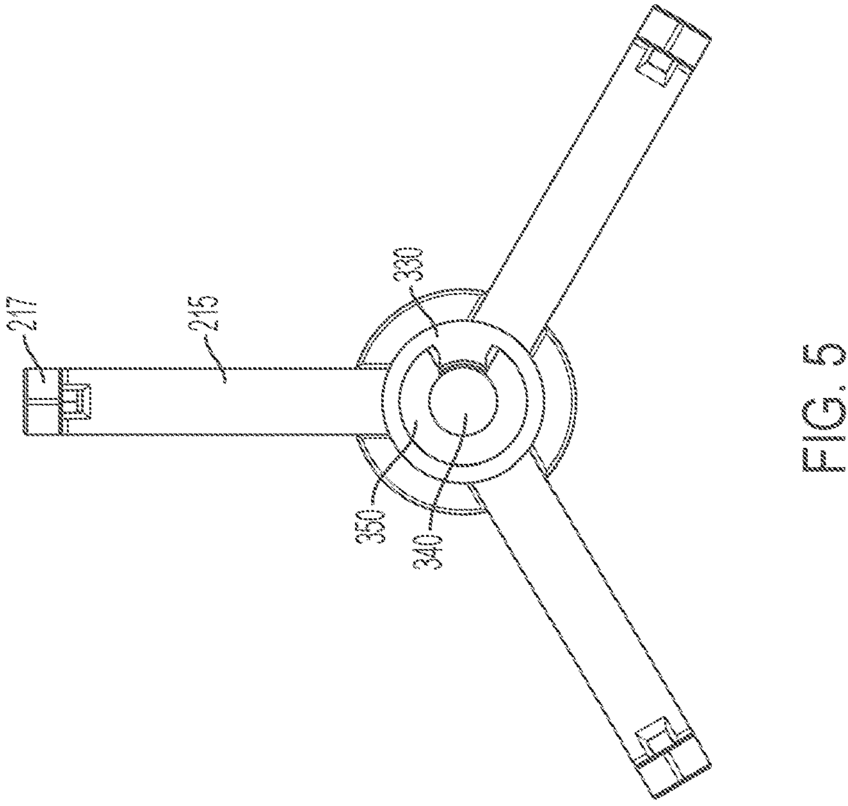
FIG. 5 is a front elevational view of the drug delivery device of FIG. 1.

As illustrated in FIG. 2, the capsule 110 is comprised of two components, a first, rear capsule portion 104 and a second, front capsule portion 106. As discussed in greater detail herein, the first capsule portion 104 and the second capsule portion 106 are coupled together to form capsule 110.

The delivery mechanism 200 is configured to fit within capsule 110 when drug delivery device 100 is assembled. In the illustrated embodiment, the delivery mechanism 200 comprises a delivery base 230, a plurality of delivery members 210 extending from the delivery base 230, a membrane 220, and a central bore 250 extending through the delivery base 230. Each delivery member 210 comprises a resilient arm 215, a delivery channel 213, an interfacing end 217, and a penetration assembly 260. In the illustrated embodiment, three delivery members 210 extend from and are circumferentially spaced equidistantly around the delivery base 230, but in other embodiments any number of delivery members 210 and spacing arrangements may be used.

Figure 12:
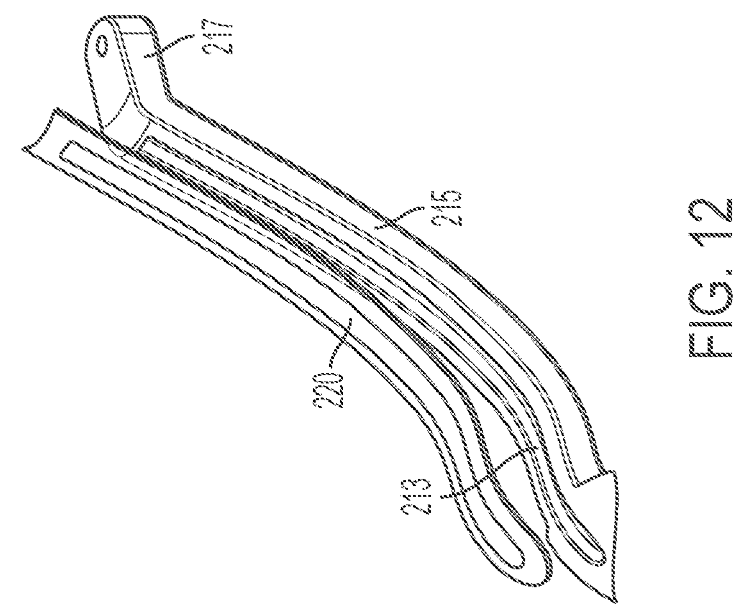
FIG. 12 is a partial exploded view of a drug delivery member of the drug delivery device of FIG. 1.

The delivery mechanism 200 is configured to allow for a fluid to flow from the central bore 250 through delivery channels 213 to interfacing ends 217. Delivery channels 213 are fluidly coupled to the central bore 250 and extend along resilient arms 215. In the illustrated embodiment, delivery channels 213 are formed as exposed grooves within an outer surface of the resilient arms 215. Referring to FIG. 12, the membrane 220 is adhered to the surface of the resilient arms 215 to enclose and seal the delivery channels 213. The membrane 220 may be adhered to the surface of the resilient arms 215 through an adhesive, welding (heat, UV, laser, ultrasonic, solvent, friction, injection, high frequency, etc.), mechanical connections, or any other connective means. The use of membrane 220 may simplify the formation (e.g., molding, cutting) of channel 213 into the outer surface of the resilient arms 215. In other embodiments, delivery channels 213 may be a separate component, such as a tube, coupled to a portion of delivery mechanism 200. Furthermore, delivery channels 213 may be located entirely within resilient arms 215, such that the interior of the delivery channels 213 is fully enclosed (e.g. a bore through resilient arm 215).

Figure 15:
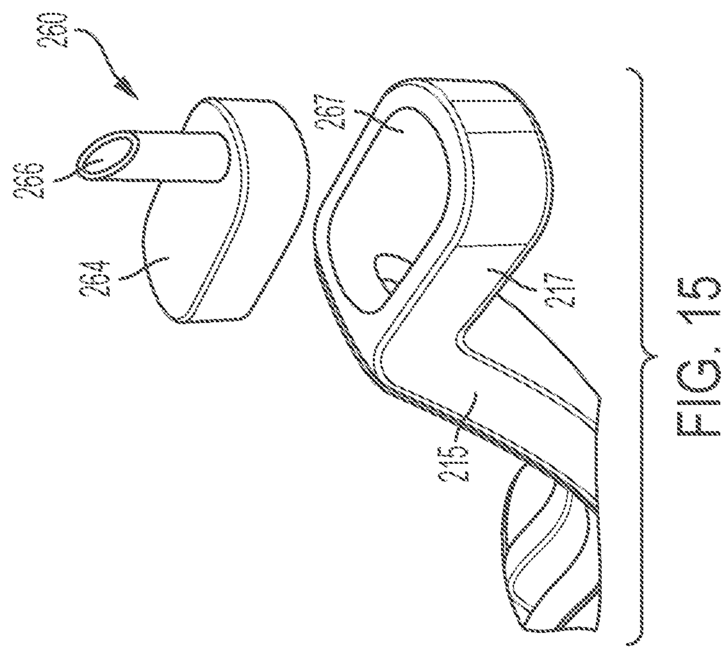
FIGS. 14-15 are partial exploded views of a GI tract wall penetrating system of the drug delivery device of FIG. 1.
Figure 14:
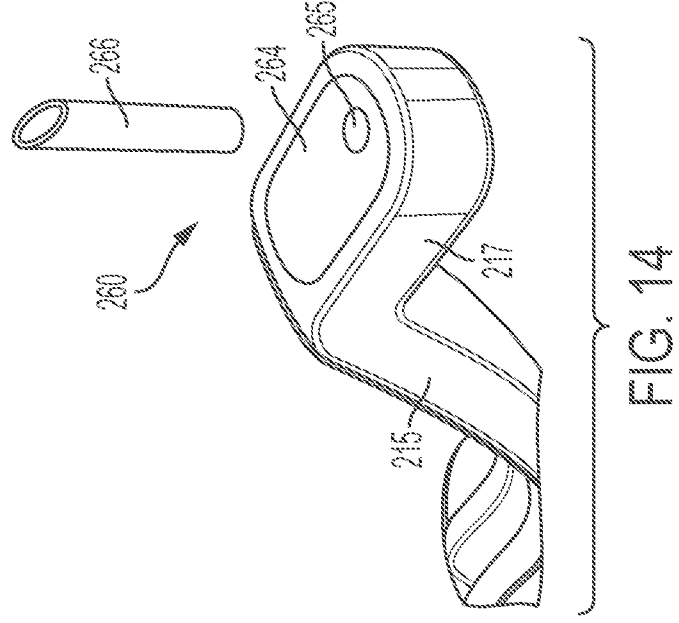

Referring to the illustrative embodiment of FIGS. 14-15, interfacing ends 217 are located near the end of each resilient arm 215 and are configured to interface with the interior of the GI tract of the patient. Interfacing ends 217 comprise a socket 267 configured to receive penetration assembly 260. Penetration assembly 260 comprises a penetration base 264 and a penetrating tip 266. As illustrated in FIG. 14, in one embodiment the penetrating tip 266 is separate from penetration base 264, and penetration base 264 comprises a receiving bore 265 configured to couple the penetration base 264 to the penetrating tip 266. In another embodiment, as illustrated in FIG. 15, the penetration base 264 and penetrating tip 266 may be formed as a single piece. Socket 267 is configured to fluidly couple each delivery channel 213 to the corresponding penetrating tip 266 such that a fluid can flow from the delivery channel 213 to the penetrating tip 266. At least one of the penetration base 264 and the penetrating tip 266 may be biodegradable. In an exemplary embodiment, the interfacing ends 217 interact with the interior wall of a GI tract and are approximately parallel to a longitudinal axis A1, and penetrating tips 266 pierce or penetrate the GI tract wall and are approximately perpendicular to axis A1. After a predetermined time has passed, the penetration base 264 and/or the penetrating tip 266 may degrade and break free from the GI tract. In the illustrated embodiment, penetrating tip 266 has the shape of a hypodermic needle. In other embodiments, penetrating tip 266 may comprise a piercing tip with a fluid outlet located below the piercing tip (e.g., in a side surface of the penetrating tip 266) to avoid blockage in the delivery of drug 500. Furthermore, each delivery member 210 may comprise any number of penetrating tips 266, including arrays of microneedles.

In an alternative embodiment, interfacing ends 217 include a liquid jet delivery mechanism for delivering the fluid through the GI tract. In this embodiment, penetration assembly 260 (e.g., element 265) is formed as a nozzle or jet that delivers the fluid from the delivery channel 213 at a high speed to puncture and penetrate the GI tract without the use of penetrating tip 266 for drug delivery. In this embodiment, driving mechanism 300, including driver 360 described herein, actuates the delivery of the drug 500 from the drug housing 400 with a high force suitable for driving the liquid jet.

Figure 13:
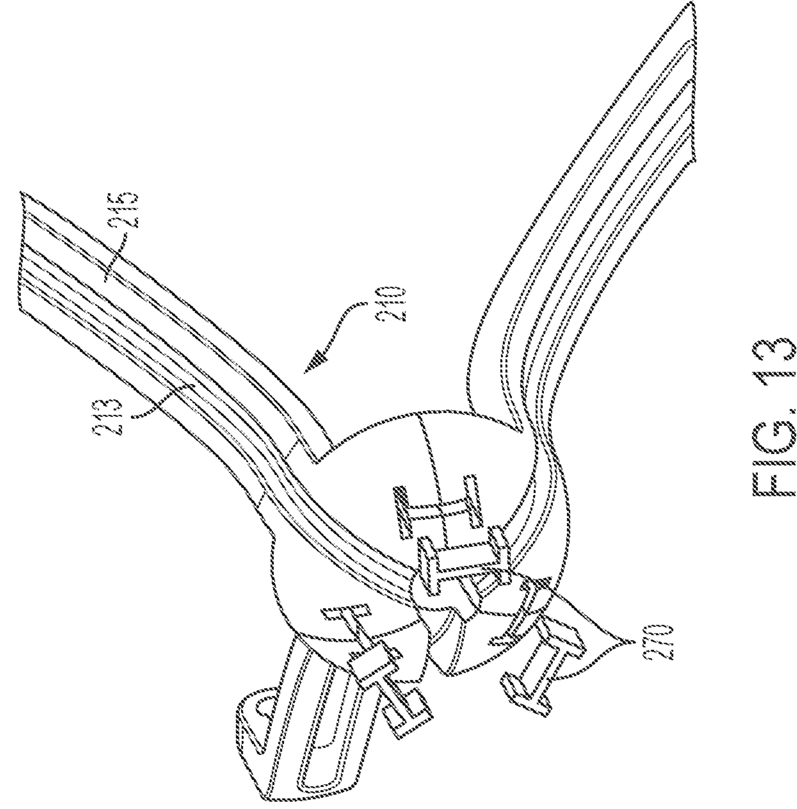
FIG. 13 is a partial exploded view of a drug delivery mechanism of the drug delivery device of FIG. 1.

Referring again to FIGS. 1-6, in the illustrated embodiment, delivery base 230 and delivery members 210 of delivery mechanism 200 are constructed as a single, integral piece. In the illustrated embodiment, delivery members 210 and delivery base 230 are resilient, having rigid, spring-like properties with delivery members 210 being adapted to flex relative to base 230, as described herein. In an exemplary embodiment, delivery mechanism 200 is adapted to dissolve or biodegrade within the intestine following delivery of the fluid. In an exemplary embodiment, delivery mechanism 200 is composed of a polymer, such as a bioresorbable/biodegradable polymer, for example. Exemplary polymers include polyglycolic acid, polylactic acid, polycaprolactone, and copolymers and blends thereof that may include polyethylene glycol. In other embodiments delivery mechanism 200 may be composed of a metal, or other suitable material. As illustrated in FIG. 13, the delivery mechanism 200 may alternatively be constructed of multiple parts connected through one or more coupling members 270. In the illustrated embodiment of FIG. 13, coupling members 270 couple a plurality of delivery members 210 together at the delivery base 230. Furthermore, in the illustrated embodiment coupling members 270 are I-shaped connectors. In other embodiments, coupling members 270 may be fasteners, screws, snaps, pins, staples, or any other mechanical coupling means. Coupling members 270 may be composed of biodegradable material, including the bioresorbable/biodegradable polymers described above, such that delivery mechanism 200 breaks into separate parts upon degradation of coupling members 270. The delivery members 210 and the coupling members 270 may both be composed of biodegradable material, or only one of the delivery members 210 and the coupling members 270 may be composed of biodegradable material. In other embodiments, any components of delivery mechanism 200 may be manufactured as separate pieces and coupled together through coupling members 270. Furthermore, components of delivery mechanism 200 may be coupled together through adhesives, welding, or other coupling means.

Referring again to FIGS. 1-6, drug housing 400 is configured to fluidly couple with delivery mechanism 200 through housing coupling 450. Drug housing 400 is further configured to hold a volume of the drug 500, generally in a liquid or otherwise flowable form. In an exemplary embodiment, the drug 500 is a compound that typically has less efficacy when taken through standard oral delivery and digestion, such as a peptide or a protein, like an insulin for example. In an illustrative embodiment, drug 500 includes one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, combined GIP/GLP-1 agonists such as tirzepatide, oxyntomodulin analogs, oxyntomodulin derivatives, therapeutic antibodies, and other suitable therapeutic agents. Drug 500 may also include a vaccine or gene-based drug. In other embodiments, drug 500 may be any biologically active compound to be administered to the patient. Drug housing 400 may be composed of a polymer, metal, ceramic, crystalline solid, or any other material capable of holding the volume of the drug 500.

Figure 17:
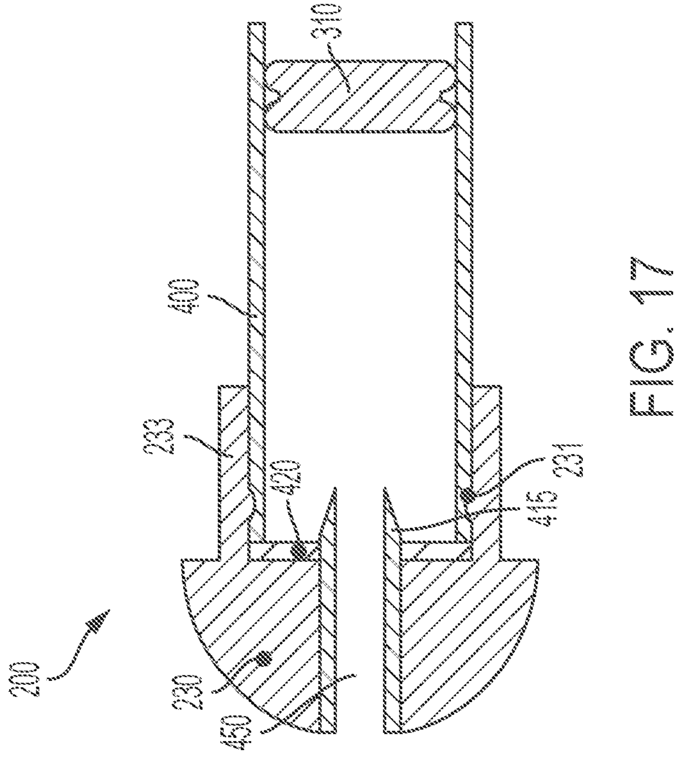
FIGS. 16-21 are simplified, cross-sectional views of the device of FIG. 1 with alternate sealing assemblies.
Figure 16:
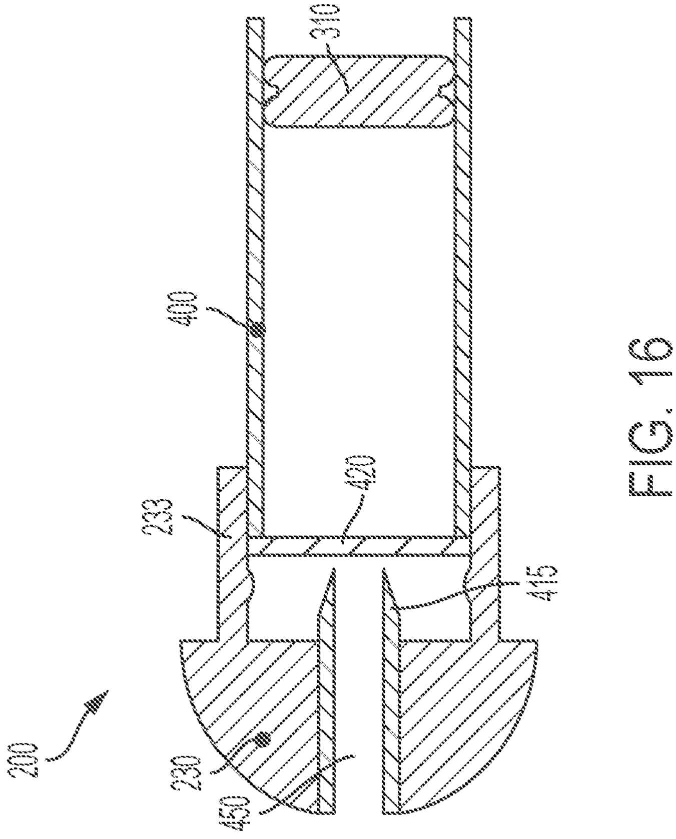

Referring to FIGS. 16-21, in alternate embodiments of drug delivery device 100 a sealing assembly may be used between drug housing 400 and delivery mechanism 200 to retain drug 500 in a sealed manner within drug housing 400 until drug 500 is ready to be introduced to delivery mechanism 200. Referring first to FIGS. 16-17, in one embodiment drug housing 400 may comprise a septum 420 which is configured to be pierced by a needle 415, similar to configurations commonly utilized by auto injection systems as is known in the art. The needle 415 can be driven to pierce the septum 420 in a priming step of the drug delivery device 100, for example when the drug delivery device 100 is assembled as shown in FIGS. 28-32. The needle 415 may also be driven through septum 420 after the drug delivery device 100 has been ingested by the patient. For example, needle 415 may be driven as a result of the capsule 110 degrading, or by the inclusion of an additional degradable or force-providing component (not shown) which can drive needle 415 upon degradation. In the illustrated embodiment, septum 420 is elastomeric and is coupled to the drug housing 400 through overmolding. In other embodiments, septum 420 may be composed of any material suitable for holding drug 500 within drug housing 400 and capable of being pierced by needle 415. Upon piercing of septum 420 with needle 415, the interior of drug housing 400 is fluidly coupled to the delivery mechanism 200 through connecting channel 450, allowing drug 500 to flow into delivery mechanism 200.

In the illustrated embodiment, delivery mechanism 200 comprises a housing sleeve 233 coupled to delivery base 230 and configured to couple the delivery mechanism 200 to housing 400. Housing sleeve 233 may be a sleeve that fits entirely around housing 400, or may comprise a number of discrete members. Housing sleeve 233 may also comprise retention features 231. Retention features 231 may be ridges, bumps, grooves, or other means for retaining housing sleeve 233 on housing 400. Housing 400 may also comprise complementary features to interface with retention features 231. Furthermore, an adhesive or other form of bonding agent may be applied to housing sleeve 233 and/or housing 400 to assist in retaining the housing sleeve 233 around housing 400.

Figure 19:
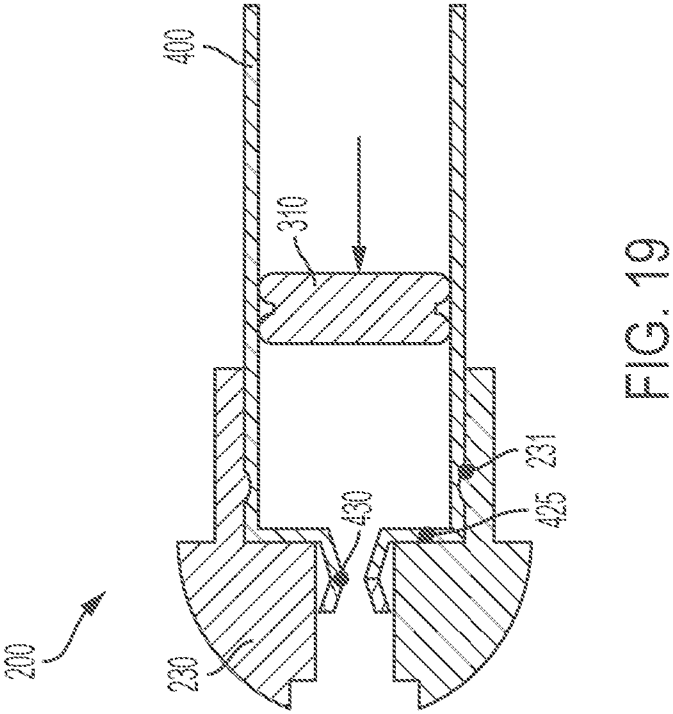
Figure 18:
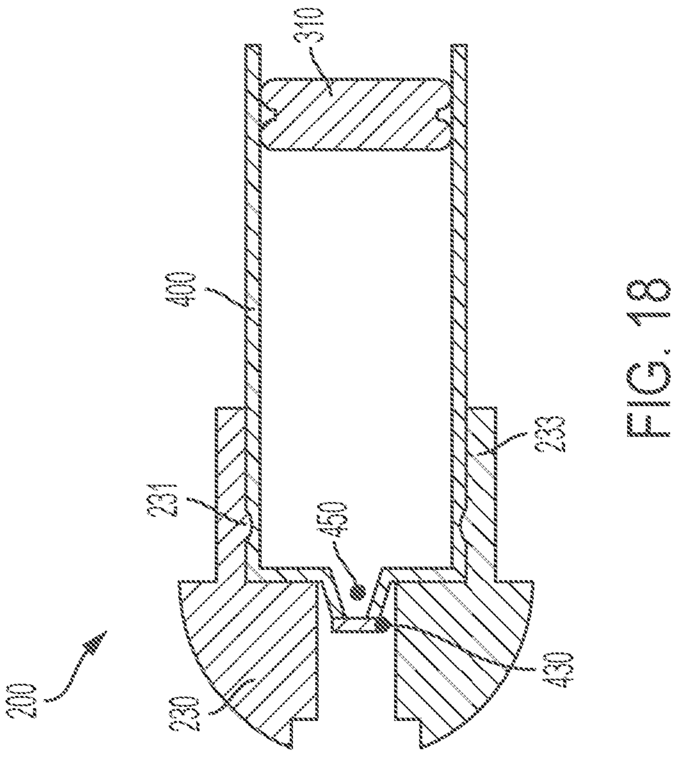

Referring now to FIGS. 18-19, in another embodiment housing 400 may comprise a breakable membrane 430 at an end of connecting channel 450. Breakable membrane 430 is configured to retain drug 500 within drug housing 400 until an increase in pressure causes the breakable membrane 430 to burst or otherwise allow passage of drug 500 through connecting channel 450. The increase in pressure may be caused by the driving of the plunger 340. In the illustrated embodiment, housing 400 interfaces with delivery base 230 at housing interface 425. Housing interface 425 is configured to contact delivery base 230 when housing sleeve 233 engages housing 400. Housing interface 425 may be coated with an adhesive or other bonding agent to assist in coupling housing 400 to delivery mechanism 200. Housing interface 425 may also comprise surface features such as ridges, bumps, grooves, or other retention features for interfacing with delivery base 230. In such embodiments, delivery base 230 may comprise complementary surface features.

Figure 21:
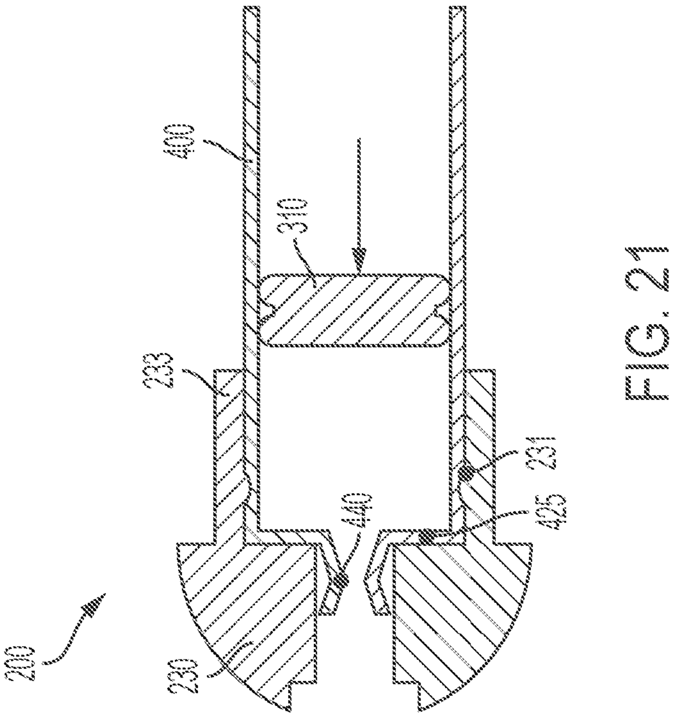
Figure 20:
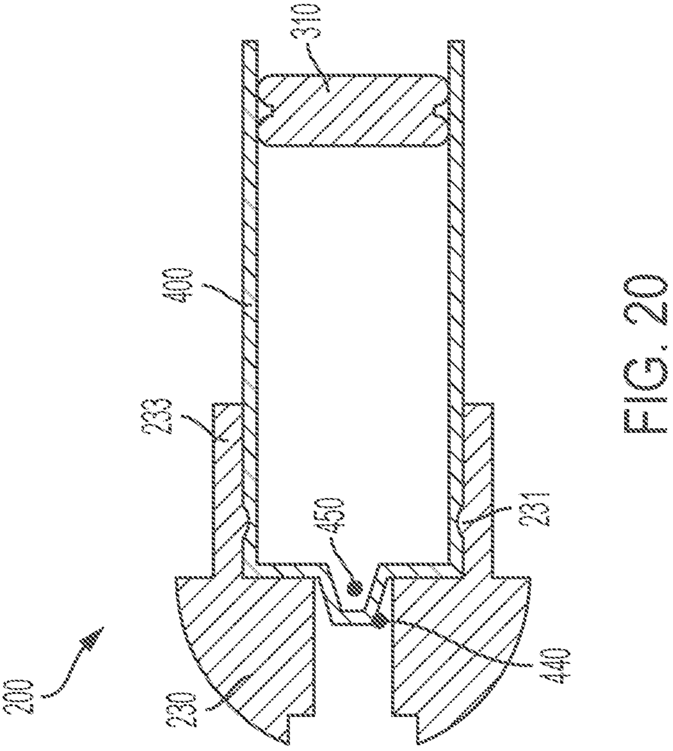

Referring to FIGS. 20-21, in yet another embodiment, housing 400 may be molded closed to form an intentional weak point 440. Weak point 440 could be burst in a similar fashion to breakable membrane 430 as described above to allow passage of drug 500 through housing coupling 450. The embodiments comprising breakable membrane 430 and/or weak point 440 may not require the priming or activation step required by the needle 415 and septum 420 configuration shown in FIGS. 16-17.

Driving mechanism 300 is configured to fit at least partially within drug housing 400, and is also configured to actuate flow of the drug 500 from the drug housing 400 into delivery mechanism 200. Driving mechanism 300 comprises a stopper 310, a plunger 340, a cap 330, a driver 360, and a trigger 350, and is arranged approximately coaxially with longitudinal axis A1. Cap 330 seals drug 500 within drug housing 400 and at least partially encloses driver 360. The plunger 340 comprises a stopper end 342 adjacent to the stopper 310 and a trigger end 344 adjacent to the trigger 350 and is movable approximately along axis A1 from a first, loaded position to a second, delivered position. At the stopper end 342 of plunger 340, plunger 340 is coupled to stopper 310. In another embodiment, plunger 340 is not coupled to stopper 310. In said embodiment, the stopper 310 is separate from the driving mechanism 300, and can be inserted into drug housing 400 before driving mechanism 300 is coupled to drug housing 400. This separation would allow for the driving mechanism 300 without stopper 310 to be assembled or manufactured separately from drug housing 400 and stopper 310, so that the driving mechanism can be coupled to drug housing 400 at a later time.

Figure 9:
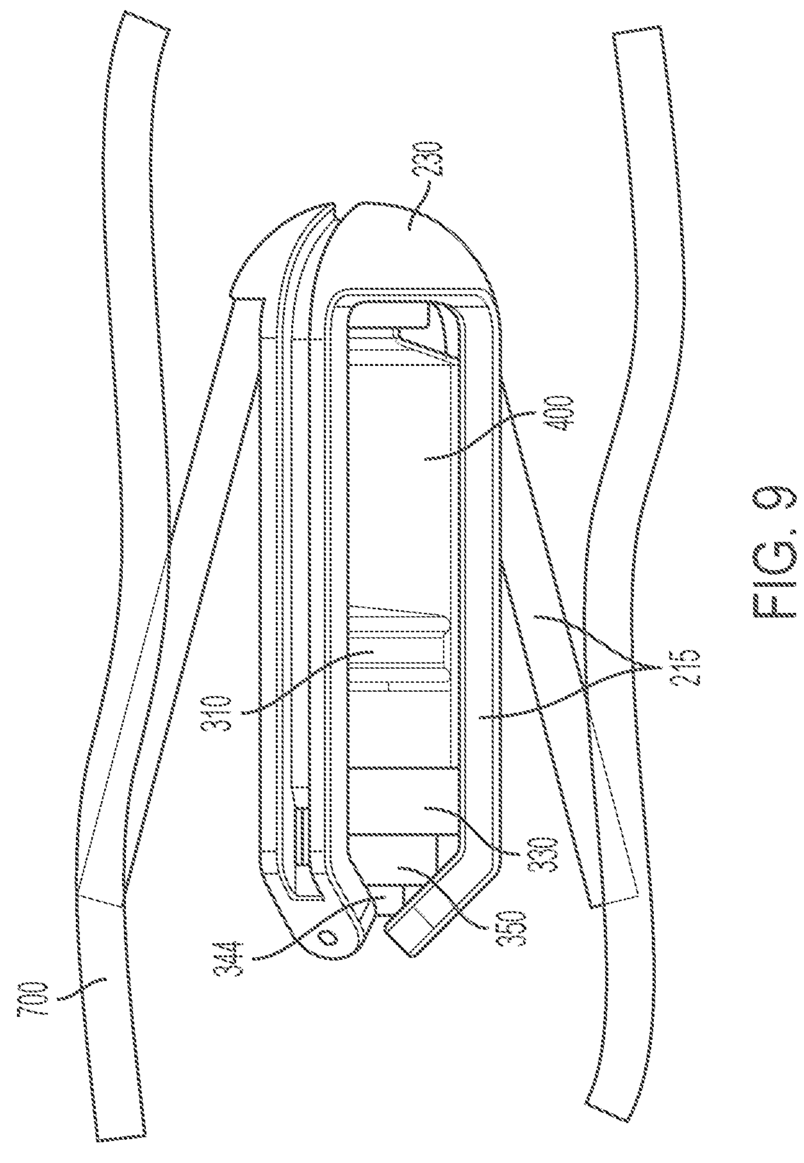
FIG. 9 is a left side view of the drug delivery device of FIG. 1 in the open configuration within a GI tract of a patient with a driving mechanism in a loaded position.
Figure 10:
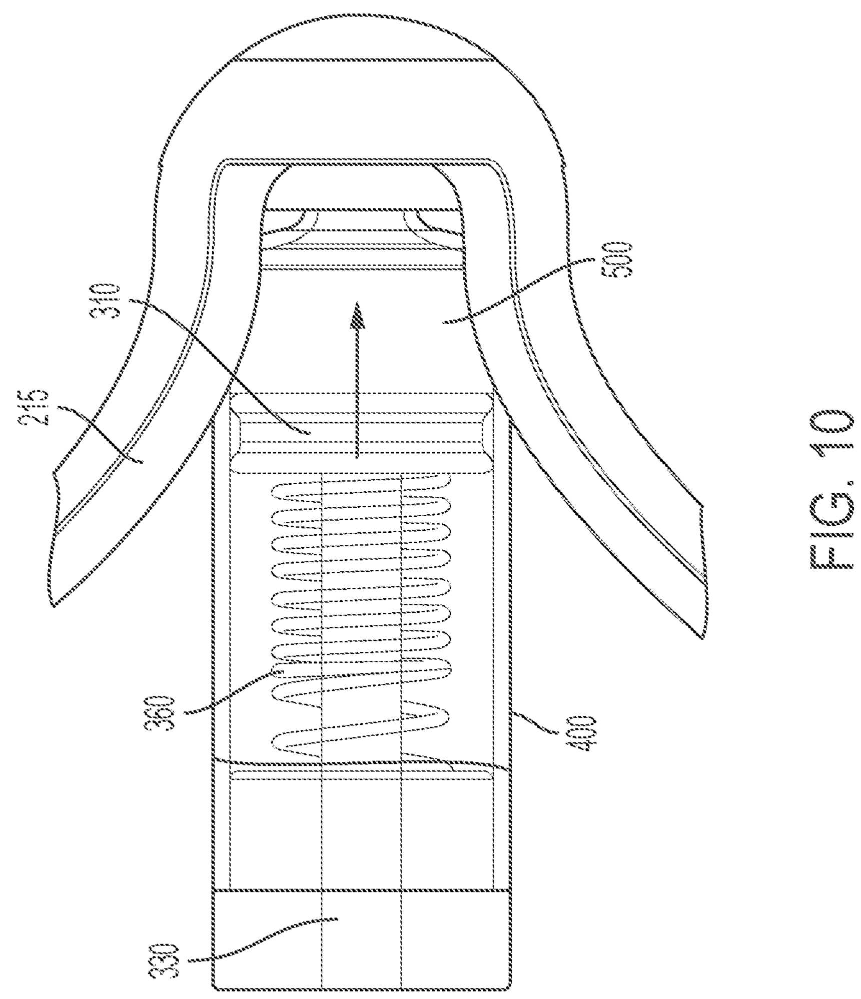
FIG. 10 is a side elevational view of the drug delivery device of FIG. 9 with the driving mechanism in a delivered position.

Referring next to FIGS. 9-10, stopper 310 is configured to seal drug 500 within drug housing 400 and is slidable approximately along axis A1. In the first, loaded position (see FIG. 9), trigger 350 is arranged between trigger end 344 and cap 330, thereby preventing trigger end 344 from passing through cap 330 and furthermore preventing the movement of plunger 340. In the first, loaded position, driver 360 applies a force to stopper end 342 approximately towards the housing coupling 450. In the illustrated embodiment, trigger 350 is composed of degradable material and is configured to degrade over time. When trigger 350 degrades and is removed from its arrangement between trigger end 344 and cap 330, the force applied to the plunger 340 by driver 360 moves the plunger 340 approximately along axis A1 to the second, delivered position (see FIG. 10). In moving from the first position to the second position, plunger 340 and stopper 310 are moved approximately toward the housing coupling 450, thereby decreasing the available volume of drug housing 400 and pushing drug 500 out of drug housing 400 into the delivery mechanism 200.

In the illustrated embodiment, driver 360 is a spring. In other embodiments, driver 360 may be any member that is capable of delivering a force to move plunger 340 from the first position to the second position, including a balloon, a piston, or a motor. In the illustrated embodiment, due to the presence of cap 330, the stopper 310, plunger 340, and driver 360 all remain within the drug housing 400 after the drug delivery device 100 has been activated and the drug 500 has been delivered. In this embodiment, the containment of the majority of the driving mechanism 300 within the drug housing 400 prevents additional, potentially damaging, components from being released into the GI tract, and instead retains the components within the relatively smooth drug housing 400 which will ultimately be passed by the patient.

Figure 22:
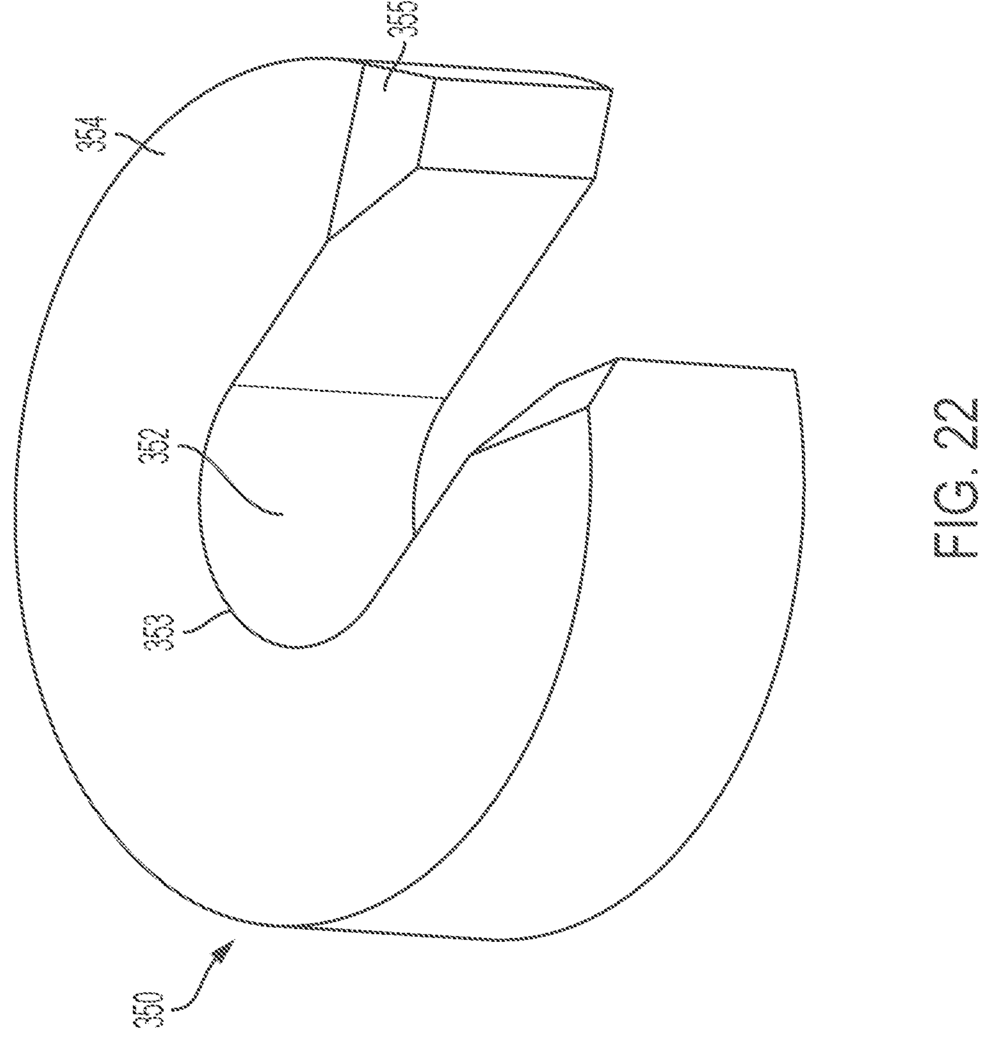
FIG. 22 is a perspective view of a trigger of the drug delivery device of FIG. 1.

Referring now to FIG. 22, trigger 350 comprises an interior 352, an interior edge 353, an upper surface 354, and at least one bevel 355. Bevel 355 may also be located at other points along the interior edge 353, and may even extend fully around interior edge 353. Furthermore, upper surface 354 may be angled downward towards the interior 352 on a portion of or the entirety of trigger 350. Plunger 340 is configured to fit within interior 352 of trigger 350. Bevel 355 along with the general horseshoe-like shape of trigger 350 is configured to direct force from driver 360 onto a smaller area of trigger 350 through trigger end 344 of plunger 340. Accordingly, trigger 350 is configured to break more readily than if trigger 350 were a solid disc. Furthermore, since many biodegradable materials do not dissolve completely in a short amount of time, the shape of trigger 350 and bevel 355 cause the trigger 350 to catastrophically fail by snapping or breaking after a threshold level of degradation has occurred. This configuration allows for driving mechanism 300 to be activated in a relatively rapid manner once the trigger 350 degrades past the threshold amount.

Figures 7, 8:
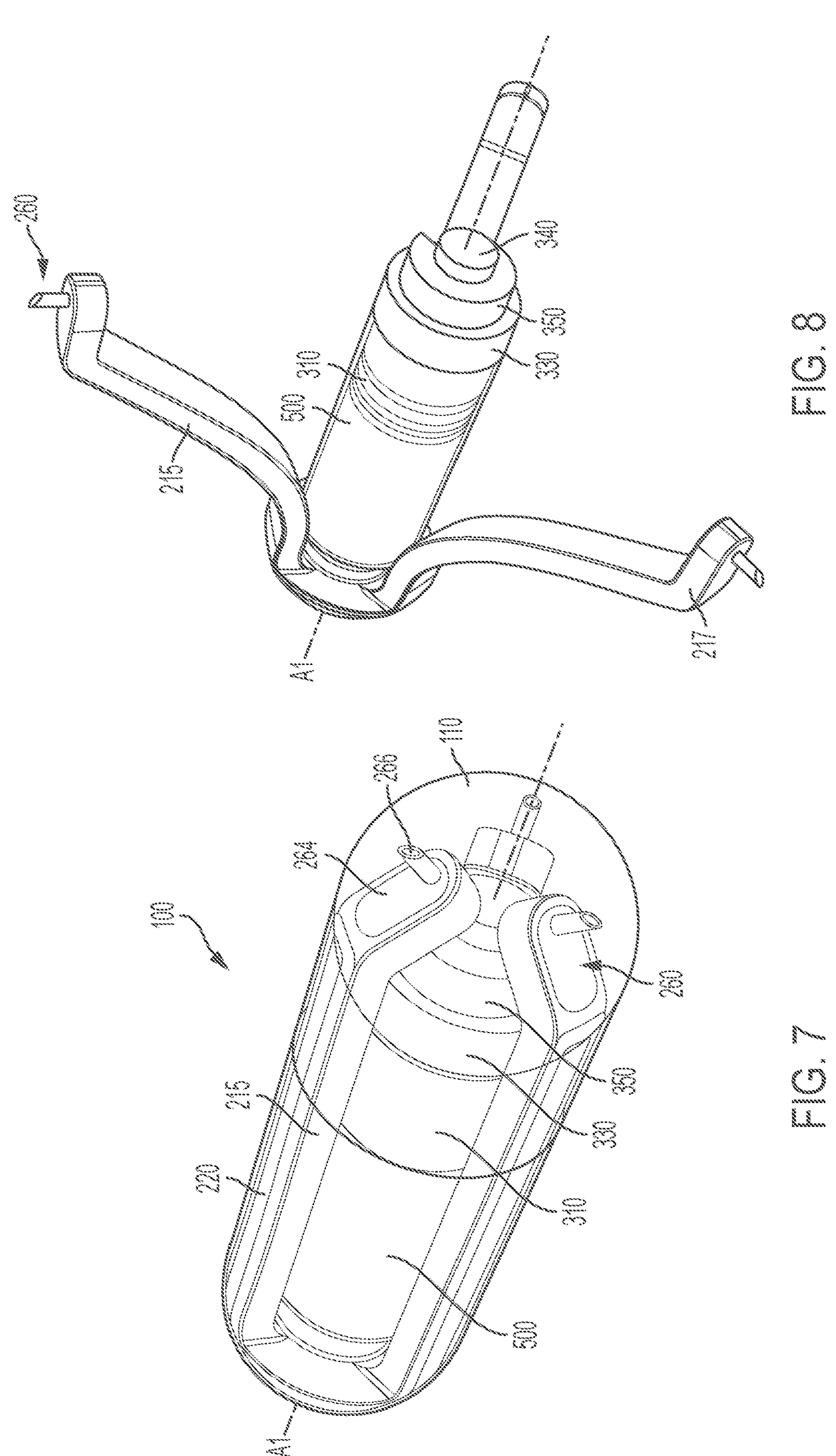
FIG. 7 is a perspective view of the drug delivery device of FIG. 1 in a closed position.
FIG. 8 is a perspective view of the drug delivery device of FIG. 7 in an open position.

Referring to FIGS. 7-8, drug delivery device 100 is movable from a first state, or a closed state (see FIG. 7), to a second state, or an open state (see FIG. 8). Delivery members 210 of delivery mechanism 200 are composed of a resilient material, such as a polymer having flexibly rigid and spring-like properties. In the illustrated embodiment, when no forces are acting upon delivery members 210, their natural state is the open state. However, delivery members 210 may be moved to the closed state, and then can spring or expand back to the second state due to the resiliency of delivery members 210. In the closed state, delivery members 210 are contained within capsule 110, lying approximately parallel to axis A1 (see FIG. 7). In the closed state, delivery members 210 exert a radially outward force on the interior of capsule 110. When capsule 110 degrades, dissolves, or otherwise breaks down past a predetermined point, delivery members 210 may break through any remaining capsule 110 and move radially outward from axis A1 to enter the open state (see FIG. 8).

When drug delivery device 100 is used to treat a patient, the patient receives drug delivery device 100 orally, and drug delivery device 100 travels through the GI tract of the patient. In an exemplary embodiment, the capsule 110 degrades as the environment around the drug delivery device 100 changes pH, for example when leaving the acidic stomach and entering the relatively alkaline small intestine. When the capsule 110 degrades by a threshold amount past the predetermined point noted above, the drug delivery mechanism 200 breaks through the capsule 110, and delivery members 210 extend outward. Within the GI tract of the patient, when the delivery members 210 extend outward the interfacing ends 217 interface with the interior of the patient's GI tract, also referred to as the GI tract wall 700. Penetrating tips 266 penetrate the GI tract wall 700, and thereby anchor the drug delivery device 100 to the wall 700 at the points of penetration (See FIG. 9). Interfacing ends 217 are configured to interface with a wall surface 710 when penetrating tips 266 penetrate the wall 700. In an embodiment using a liquid jet delivery, the spring-force of the delivery members 210 against the wall 700 may be configured to provide sufficient anchoring force to deliver the drug. Additionally or alternatively, ends 217 may include interfacing features such as penetrating tips or ridges for gripping and anchoring the device 100 to the wall 700 during liquid jet delivery.

Figure 11:
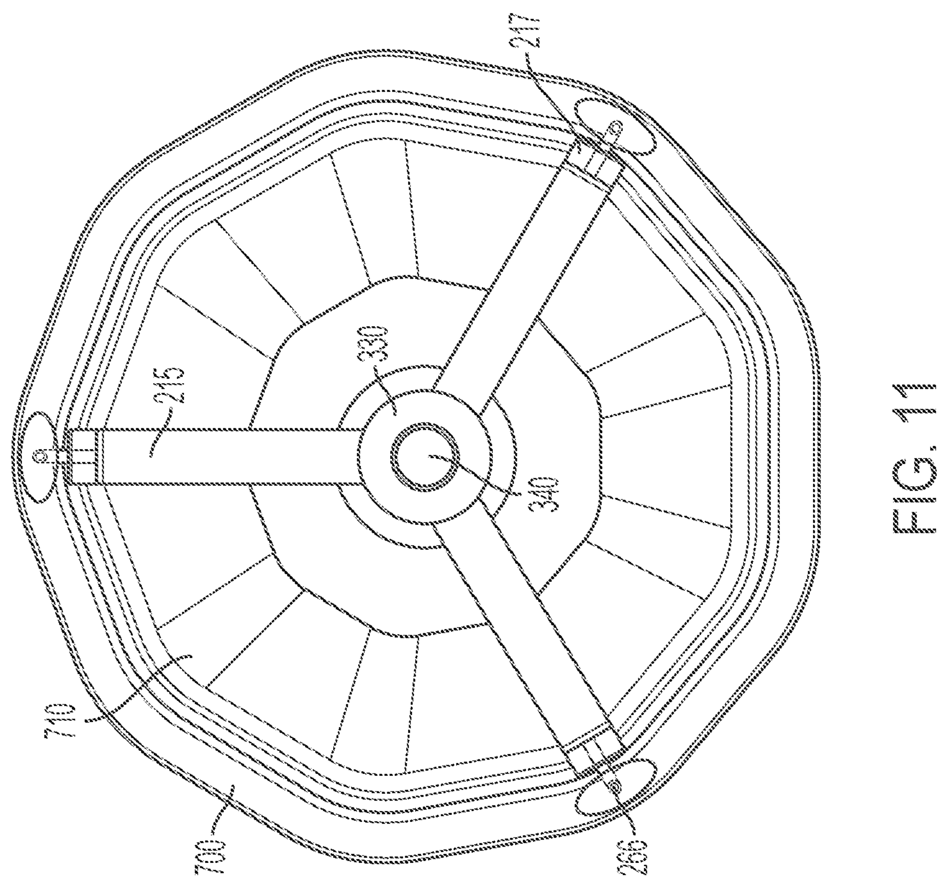
FIG. 11 is a front elevational view of the drug delivery device of FIG. 1 in the open configuration and delivering a drug to the GI tract of the patient.

After the drug delivery device 100 has penetrated the GI tract wall 700, trigger 350 degrades past a threshold, allowing driver 360 to drive plunger 340 and stopper 310 into the drug housing 400, pushing drug 500 through the delivery mechanism 200 (see FIG. 10), and into the wall 700 through penetrating tips 266 (see FIG. 11). After the drug 500 has been delivered to the patient through penetrating tips 266, penetrating assembly 260 will degrade. After penetrating assembly 260 has degraded past a threshold, delivery mechanism 200 will break or release from penetrating assembly 260 and will be passed through the GI tract. Other components of the delivery mechanism 200 may also break apart upon degradation of coupling members 270, as described above. In some embodiments, the components of delivery mechanism 200 made of the biodegradable/bioresorbable polymer (described herein) are also adapted to degrade and dissolve following delivery of the drug.

Figure 23:
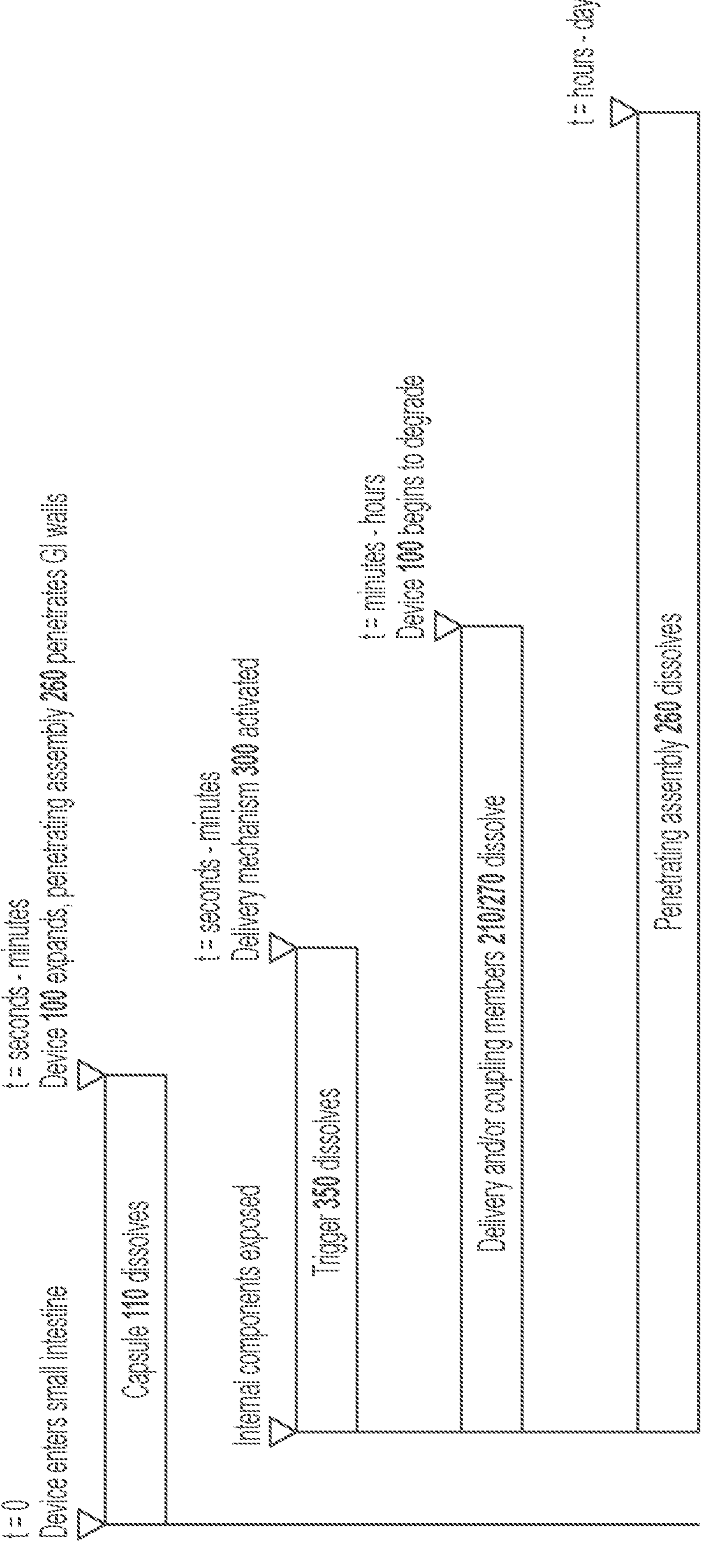
FIG. 23 is an exemplary timeline of the degradation of the device of FIG. 1.
Figure 24:
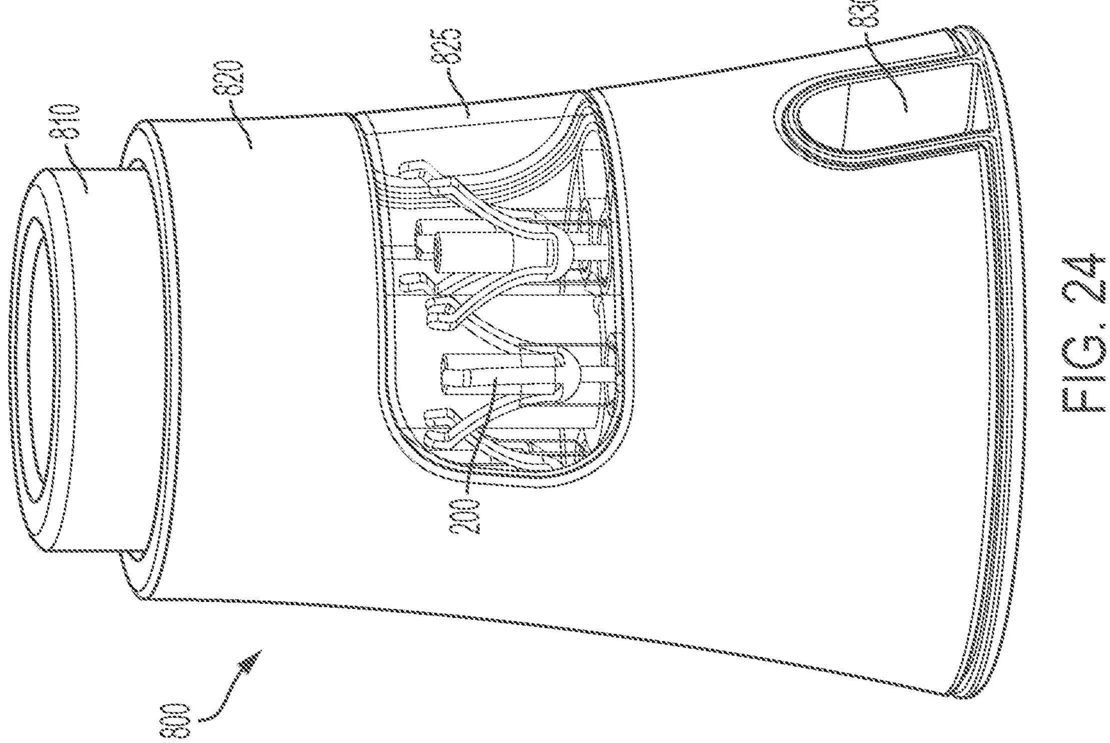
FIG. 24 is a perspective view of an assembly mechanism for use with the drug delivery device of FIG. 1.
Figure 26:
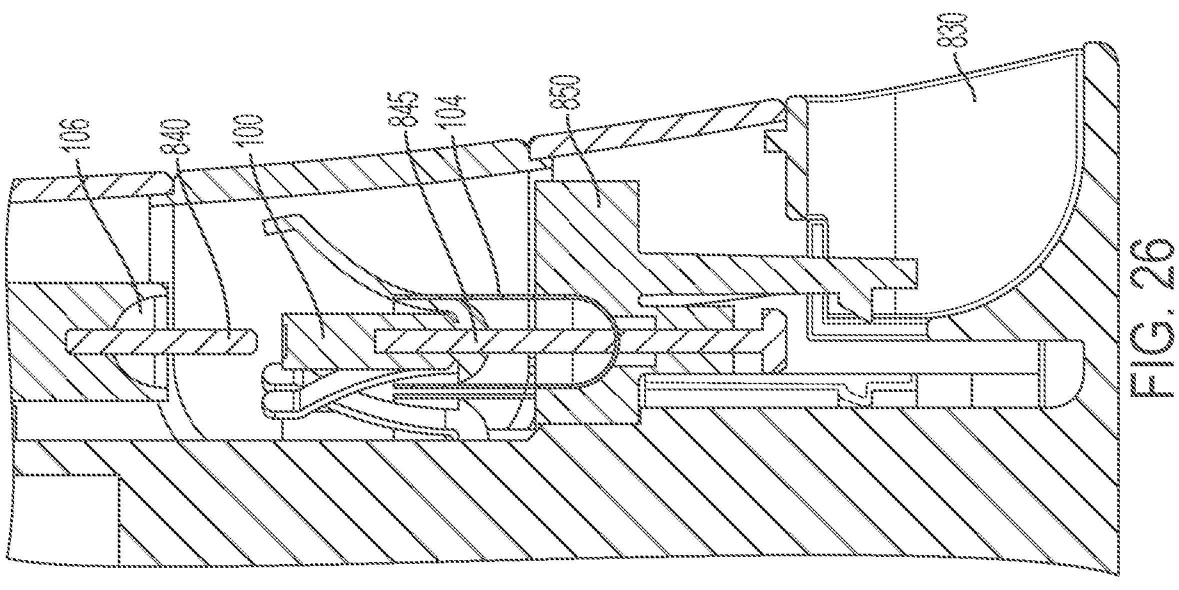
FIGS. 25-26 are a cross sectional view and a partial cross-sectional view, respectively, of the assembly mechanism of FIG. 12
Figure 25:
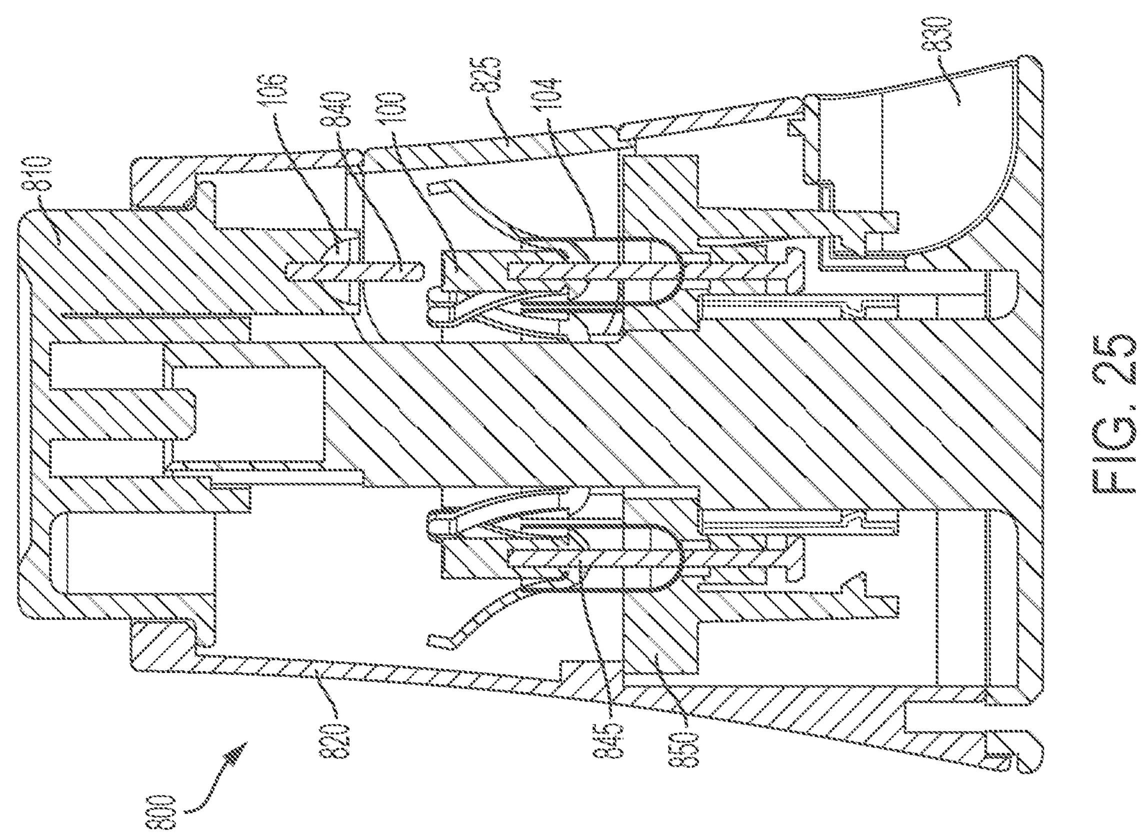
Figure 27:
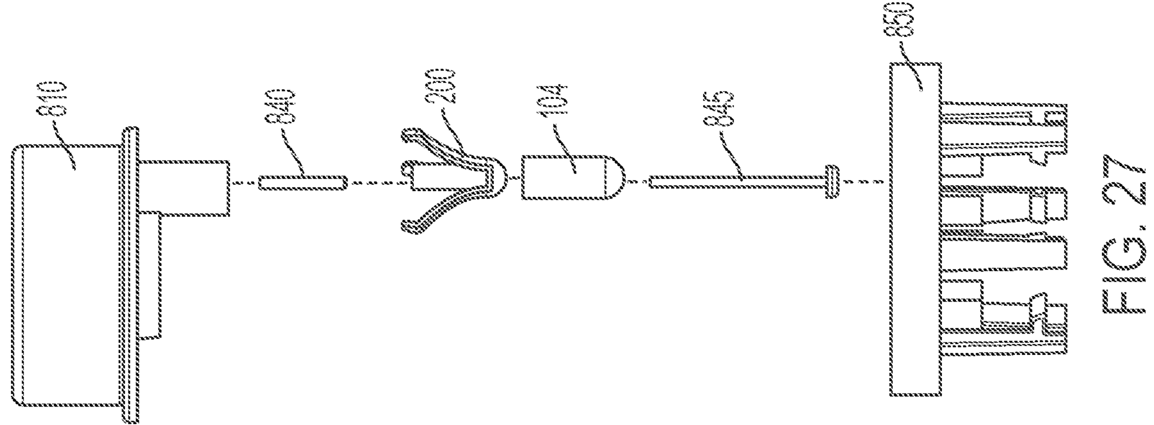
FIG. 27 is a partial exploded view of a number of the internal components of the assembly mechanism of FIG. 12.
Figures 28, 29, 30, 31, 32:
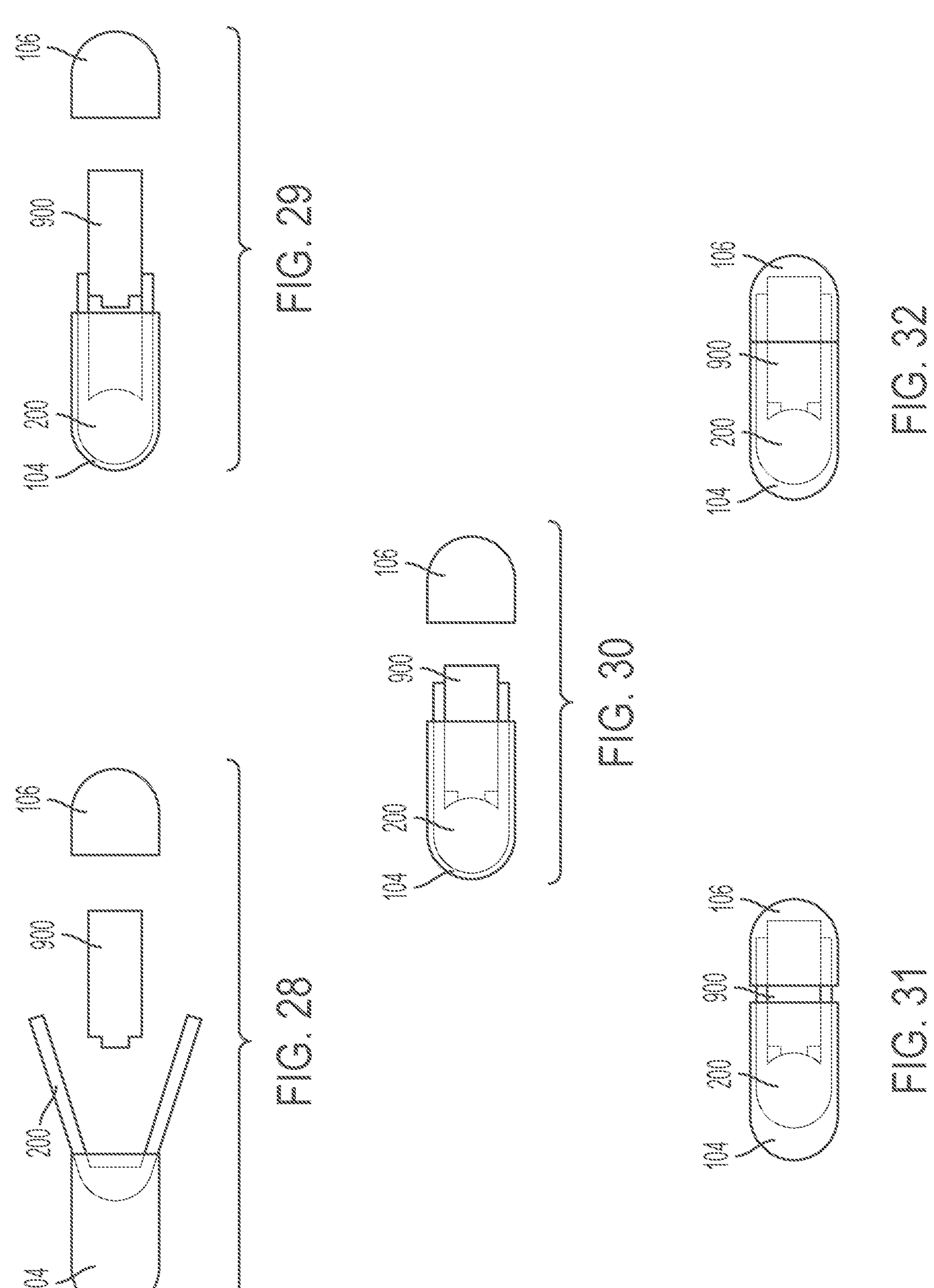
FIGS. 28-32 are depictions of a method of assembling the drug delivery device of FIG. 1.

Referring to FIG. 23, a depiction of the relative degradation times of different components of drug delivery device 100 is shown according to one exemplary embodiment. In the illustrated embodiment, the first component to degrade is the capsule 110, exposing the internal components of the device 100 and allowing the device 100 to spring open and position itself within the GI tract. The next component to degrade is the trigger 350, thereby activating the delivery mechanism 300 and delivering the drug 500 to the patient. The next component to degrade is the delivery members 210 and/or coupling members 270, thereby allowing the drug delivery device 100 to pass through the remainder of the GI tract and be passed by the patient. Finally, the penetrating assembly 260, or specific components within penetrating assembly 260, degrade. The capsule 110 and trigger 350 both degrade on approximately a scale of minutes or seconds. The delivery members 210 and/or coupling members 270 degrade approximately on a scale of hours. The penetrating assembly 260 or its components degrade approximately on a scale of hours or days. Components of drug delivery device 100 may be designed to degrade on other suitable time scales in other embodiments.

In an exemplary embodiment, delivery mechanism 200 comprises a pressure regulator (not shown). When penetrating tips 266 penetrate the GI tract wall 700, an interstitial pressure is created at the wall surface 710. For the drug 500 to transfer across the GI tract wall surface 710, driver 360 must generate a pressure within the drug 500 greater than the interstitial pressure so that drug 500 flows through the wall 700. The pressure regulator sets a pressure threshold greater than the interstitial pressure in each delivery member 210 such that the driver 360 must generate a pressure within the drug 500 greater than the pressure threshold so that the drug 500 flows through the delivery members 210. Accordingly, in the event that one or more of the penetrating tips 266 does not penetrate the wall 700, the disengaged penetrating tips 266 that did not penetrate the wall 700 will still be subject to the pressure threshold set by the pressure regulator, so a portion of drug 500 will still be delivered through the engaged penetrating tips 266 that did penetrate the wall 700. In the absence of the pressure regulator, a majority of the drug 500 would escape through the penetrating tip(s) 266 that did not penetrate the wall 700, since they would provide a path of lesser resistance.

In another embodiment, only one of the delivery members 210 may contain a delivery channel 213, and accordingly only that one delivery member 210 would be capable of delivering the drug 500 to the patient. The other delivery members 210 may be configured to serve as "dummy" or structural delivery members 210, and may be present to assist in securing the drug delivery device 100 within the GI tract without serving as a means for delivering the drug 500. Said structural delivery members 210 may not include a penetration assembly 260, since no drug 500 would be flowing through said delivery members 210 to then flow through penetration assembly 260. Structural delivery members 210 may comprise interfacing features (not shown) on the interfacing ends 217 in order to grip the GI tract wall 700. Such interfacing features may include ridges, protrusions, adhesives, or other gripping/attachment means. Structural delivery members 210 may also comprise microneedles, patches, solid drug deposits, or other drug delivery means to allow diffusion of a drug or other active agent through the wall 700 without penetration.

Referring to FIGS. 24-27, in order to reduce the likelihood of viscoelastic creep within delivery mechanism 200, a device assembly mechanism 800 is provided. In an exemplary embodiment, a user or patient could receive device assembly mechanism 800 and assemble the drug delivery device 100 soon before orally ingesting the drug delivery device 100. Device assembly mechanism 800 comprises an assembly housing 820, an assembly actuator 810, access window 825, rotating member 850, first driving rod 840, second closing rod 845, and device retrieval area 830. Assembly actuator 810 is configured to be pressed or otherwise activated by a user to initiate assembly of a single drug delivery device 100 at a time. In the illustrated embodiment, device assembly mechanism 800 is loaded with a number of drug delivery devices 100. First capsule portions 104 and the interior components of drug delivery devices 100 (specifically, delivery mechanisms 200, driving mechanism 300, drug housing 400, and drug 500) are held in rotating member 850, and second capsule portions 106 are held in actuator 810. In the illustrated embodiment, access window 825 may be removed to allow for additional loading of device assembly mechanism 800. When the assembly actuator 810 is activated, first driving rod 840 drives the interior components of drug delivery device 100 into the first capsule portion 104. First driving rod 840 also brings the second capsule portion 106 into contact with the first capsule portion 104. The second capsule portion 106 and first capsule portion 104 may be coupled by friction, welding, adhesives, mechanical fasteners, or other coupling means. Once the capsule 110 is fully formed around the interior components of drug delivery device 100, second closing rod 845 releases the drug delivery device 100 from rotating member 850 and causes the drug delivery device to enter device retrieval area 830. This process may be repeated before the patient orally ingests each drug delivery device 100.

Referring to FIGS. 28-32, an exemplary embodiment of a device assembly process is depicted. Drug housing 400 and driving mechanism 300 are combined and simplified in the drug driving unit 900. Delivery mechanism 200 is pushed into first capsule portion 104 and enters a closed state wherein the delivery members 210 partially enclose drug driving unit 900. Drug driving unit 900 is pushed further into delivery mechanism 200 so that the drug driving unit 900 and the delivery mechanism are fluidly coupled. The second capsule portion 106 is then pushed over drug driving unit 900 and delivery mechanism 200, and then sealed to first capsule portion 104.

In another embodiment, drug delivery device 100 may comprise a wireless communication device configured to send and/or receive signals to/from a wireless receiver (not shown). The wireless communication device may be configured to measure or sense biological information within the patient after drug delivery device 100 has been ingested. For example, the wireless receiver may send a signal when the delivery mechanism 200 has expanded, or when a portion of drug delivery device 100 has degraded. Furthermore, the wireless communication device may measure/sense other biological information within the GI tract, such as chemical concentrations, pH, temperature, or other biological information. The wireless receiver may be used by the patient receiving treatment, or by another user such as a physician or caretaker. The wireless communication device and wireless receiver may communicate through RFID, magneto-acoustics, near field communications, ultrasonic waves, Bluetooth technology, or other wireless communication means.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A drug delivery device comprising:

a capsule configured to degrade within a gastrointestinal (GI) tract of a patient;

a drug delivery mechanism within the capsule and configured to interact with a GI tract wall of the patient, the drug delivery mechanism comprising a plurality of resilient arms, a plurality of wall interfacing ends, and a plurality of drug delivery channels, wherein the plurality of wall interfacing ends are fluidly coupled to the plurality of drug delivery channels;

a drug housing fluidly coupled to the drug delivery mechanism and configured to contain a volume of a drug; and a driving mechanism configured to fit at least partially within the drug housing, the driving mechanism comprising a stopper positioned with-in the drug housing, a trigger, and a driver configured to apply a force to move the stopper in response to an activation by the trigger, wherein the driving mechanism actuates delivery of the drug through the drug delivery mechanism.

2. The drug delivery device of claim 1, wherein the capsule is configured to degrade after entering a small intestine of a patient.

3. The drug delivery device of claim 1, wherein the drug delivery mechanism is configured to transition from a closed position to an open position after the capsule degrades, wherein the drug delivery mechanism expands radially outward to interact with the GI tract wall of the patient in the open position.

4. The drug delivery device of claim 3, wherein the plurality of wall interfacing ends include penetrating tips, and the penetrating tips are configured to penetrate the GI tract wall when the drug delivery mechanism is in the open position.

5. The drug delivery device of claim 3, wherein the plurality of wall interfacing ends include at least one liquid jet configured to deliver the drug as a jet stream through the GI tract wall.

6. The drug delivery device of claim 3, wherein the trigger is dissolvable within the gastrointestinal tract of the patient and degrades after the drug delivery mechanism is in the open position, the driving mechanism being activated when the trigger degrades.

7. The drug delivery device of claim 1, wherein the wall interfacing ends include penetrating tips that are dissolvable needle structures, the dissolvable needle structures configured to pierce the GI tract wall of the patient and to degrade within the gastrointestinal tract of the patient.

8. The drug delivery device of claim 1, wherein the resilient arms are coupled together through a plurality of dissolvable coupling members, the dissolvable coupling members configured to degrade within the gastrointestinal tract of the patient.

9. The drug delivery device of claim 1, further comprising a channel membrane, wherein each of the plurality of drug delivery channels is formed within a corresponding resilient arm, and the channel membrane separates an interior of the plurality of drug delivery channels from the gastrointestinal tract of the patient.

10. The drug delivery device of claim 1, further comprising a membrane within the drug housing, the membrane comprising a sealed configuration in which the membrane retains the drug within the drug housing, and an open configuration in which the membrane at least partially opens and permits flow of the drug out of the drug housing.

11. The drug delivery device of claim 1, further comprising a cap coupled to the drug housing, wherein the cap blocks the driving mechanism from exiting the drug housing and entering the GI tract.

12. The drug delivery device of claim 1, wherein at least one component of the drug delivery mechanism degrades after the driving mechanism actuates delivery of the drug.

13. The drug delivery device of claim 12, wherein the drug delivery mechanism further comprises a plurality of coupling members, the coupling members configured to degrade within the GI tract.

14. The drug delivery device of claim 1, wherein the stopper is coupled to the drug housing separately from the driver and the trigger.

15. The drug delivery device of claim 1, wherein the drug delivery mechanism is composed of a biodegradable polymer including at least one of a polyglycolic acid, a polylactic acid, and a polycaprolactone.

16. The drug delivery device of claim 1, further comprising the drug contained within the drug housing, the drug including at least one of a GLP-1 receptor agonist, a GIP, a GIP analog, a GIP derivative, a combined GIP/GLP-1 agonist, tirzepatide, and glucagon.

17. An assembly system to assemble the drug delivery device of claim 1, the assembly system comprising:

an assembly system housing;

an assembly actuator coupled to the housing and configured to be actuated by a user;

a rotating member within the housing configured to hold a first portion of the capsule;

a driving rod configured to drive the drug delivery mechanism, the drug housing, and the driving mechanism at least partially within the first portion of the capsule when the assembly actuator is activated; and a closing rod configured to couple a second portion of the capsule to the first portion of the capsule, thereby enclosing the drug delivery mechanism, the drug housing, and the driving mechanism completely within the capsule.

18. A drug delivery device comprising:

a degradable capsule;

a drug delivery mechanism located within the degradable capsule comprising a fluid channel and a plurality of drug delivery members;

a drug housing fluidly coupled to the fluid channel configured to hold a volume of a drug; and a driving mechanism coupled to and located at least partially within the drug housing, the driving mechanism comprising:

a drug housing cap configured to fluidly seal the drug housing;

a driving rod slidable within the drug housing;

a driving stopper coupled to the driving rod configured to interface with the drug;

a driver within the drug housing cap and coupled to the driving rod; and a dissolvable trigger configured retain the driving rod in a first position, wherein the driver pushes the driving rod from the first position to a second position when the dissolvable trigger degrades, the drug being released through the drug delivery mechanism when the driving rod moves from the first position to the second position.

19. The drug delivery device of claim 18, wherein the degradable capsule is configured to degrade after a pH change occurs in an environment surrounding the degradable capsule.

20. The drug delivery device of claim 18, wherein each of the plurality of drug delivery members comprise a resilient arm and a wall interfacing end, the wall interfacing end including at least one liquid jet configured to deliver the drug as a jet stream through the GI tract wall.

21. The drug delivery device of claim 18, wherein each of the plurality of drug delivery members comprise a resilient arm and a penetrating tip, the penetrating tip configured to penetrate a GI tract wall of a small intestine of a patient.

22. The drug delivery device of claim 21, wherein the penetrating tip comprises a needle and a degradable base, the degradable base coupled to the resilient arm and the needle coupled to the degradable base.

23. The drug delivery device of claim 21, wherein the penetrating tip comprises a degradable needle, the degradable needle configured to degrade after penetrating the GI tract wall of the small intestine of the patient.

24. The drug delivery device of claim 18, wherein the dissolvable trigger comprises a bevel, the bevel configured to weaken the structure of the dissolvable trigger as the dissolvable trigger degrades.

25. The drug delivery device of claim 18, wherein the fluid channel is located within one of the drug delivery members, and a remainder of the drug delivery members are structural drug delivery members, the structural drug delivery members configured to position the drug delivery device within a gastrointestinal tract of a patient.

26. An oral drug delivery device comprising:

a housing capsule;

a drug delivery mechanism within the housing capsule comprising:

at least one drug delivery member configured to interact with a wall of a gastrointestinal (GI) tract of a patient; and a fluid channel within the at least one drug delivery member configured to allow a drug to flow through the drug delivery member, wherein a fluid resistance within the fluid channel is greater than an interstitial resistance from an interaction with the wall of the gastrointestinal tract;

a drug housing coupled to the drug delivery mechanism; and a driving mechanism configured to drive a drug from the drug housing to the drug delivery mechanism.

27. The drug delivery device of claim 26, wherein the drug delivery mechanism is at least partially composed of a resilient polymer configured to transition from a first position to a second position, the at least one drug delivery member configured to interact with the wall when the drug delivery mechanism is in the second position.

28. A method for treatment with the oral drug delivery device of claim 26, comprising:

loading an unassembled oral drug delivery device into an assembly mechanism;

actuating the assembly mechanism, the assembly mechanism configured to insert the drug delivery mechanism within a first portion of the housing capsule, and to couple a second portion of the housing capsule to the first portion of the housing capsule;

receiving the oral drug delivery device from the assembly mechanism; and orally consuming the drug delivery device.

29. The oral drug delivery device of claim 26, wherein the driving mechanism comprises a dissolvable trigger, the dissolvable trigger configured to degrade after the drug delivery mechanism is at least partially removed from the housing capsule.

30. The oral drug delivery device of claim 26, wherein the drug delivery mechanism is configured to expand and anchor the drug delivery mechanism within the wall of the gastrointestinal tract.

31. The oral drug delivery device of claim 26 further comprising a coupling channel positioned between the drug housing and the delivery mechanism and a weak point within the coupling channel, the weak point configured to break after a threshold pressure is applied to the weak point.

32. An oral drug delivery device comprising:

a biodegradable capsule;

a plurality of arms; and a liquid drug;

wherein the oral drug delivery device has:

a closed configuration in which the plurality of arms is disposed within the capsule;

an open configuration in which the plurality of arms extend radially outward upon degradation of the capsule to contact a patient;

a delivered configuration in which the liquid drug is injected through the plurality of arms and into the patient; and a released configuration in which the plurality of arms is separated from the patient to pass through the patient.

33. The oral drug delivery device of claim 32, further comprising a needle and a septum, wherein the oral drug delivery device has (1) an unprimed configuration in which the needle does not contact the septum, and (2) a primed configuration in which the needle pierces the septum.

34. The oral drug delivery device of claim 32, further comprising a trigger and a plunger positioned within the capsule, and a bevel on the trigger, wherein the oral drug delivery device transitions to the delivered configuration after the trigger at least partially degrades and the plunger moves across the bevel.

35. A method for delivering a drug to a patient through a drug delivery device comprising:

administering the drug delivery device orally to the patient;

degrading a capsule within a small intestine of the patient;

expanding a delivery mechanism having a plurality of ends to interface with the small intestine of the patient after the degrading step;

engaging a wall of the small intestine of the patient with a penetration assembly disposed on an end of the delivery mechanism;

degrading a trigger of the drug delivery device;

delivering the drug to the patient through the delivery mechanism; and degrading the delivery mechanism.

36. The method of claim 35, wherein the penetration assembly includes a liquid jet configured to deliver the drug as a jet stream that penetrates the wall of the small intestine.

37. The method of claim 35, wherein the engaging step includes penetrating the small intestine of the patient with a plurality of penetrating tips disposed on the ends of the delivery mechanism.

38. The method of claim 35, wherein the degrading step further includes degrading the delivery mechanism.

* * * * *